US007917223B2

(12) United States Patent
Madjar et al.

(10) Patent No.: US 7,917,223 B2
(45) Date of Patent: Mar. 29, 2011

(54) SELF POWERED OSTEOGENESIS AND OSSEOINTEGRATION PROMOTION AND MAINTENANCE DEVICE FOR ENDOSSEOUS IMPLANTS

(75) Inventors: David Madjar, Ramat Gan (IL); Menachem Nathan, Tel Aviv (IL); Emanuel Peled, Even Yehuda (IL); Hanan Terkel, Ramat Gan (IL)

(73) Assignee: Cellectric Medical, Ltd., Netanya (IL)

( * ) Notice: Subject to any disclaimer, the term of this patent is extended or adjusted under 35 U.S.C. 154(b) by 1139 days.

(21) Appl. No.: 10/543,595

(22) PCT Filed: Jan. 29, 2004

(86) PCT No.: PCT/IL2004/000092
§ 371 (c)(1),
(2), (4) Date: May 1, 2006

(87) PCT Pub. No.: WO2004/066851
PCT Pub. Date: Aug. 12, 2004

(65) Prior Publication Data
US 2006/0265026 A1   Nov. 23, 2006

(30) Foreign Application Priority Data

Jan. 29, 2003   (IL) .......................................... 154184

(51) Int. Cl.
*A61N 1/18* (2006.01)
(52) U.S. Cl. ....................................................... 607/51
(58) Field of Classification Search ................... 607/51; 433/172, 173, 174, 175, 176
See application file for complete search history.

(56) References Cited

U.S. PATENT DOCUMENTS

| 4,026,304 | A |   | 5/1977  | Levy            |          |
|-----------|---|---|---------|-----------------|----------|
| 4,027,392 | A | * | 6/1977  | Sawyer et al.   | 433/174  |
| 4,105,017 | A |   | 8/1978  | Rayaby et al.   |          |
| 4,244,373 | A |   | 1/1981  | Nachman         |          |
| 4,430,999 | A |   | 2/1984  | Brighton et al. |          |
| 4,467,808 | A |   | 8/1984  | Brighton et al. |          |
| 4,509,520 | A |   | 4/1985  | Dugot           |          |
| 4,549,547 | A |   | 10/1985 | Brighton et al. |          |
| 4,781,591 | A | * | 11/1988 | Allen           | 433/174  |
| 5,030,236 | A |   | 7/1991  | Dean            |          |
| 5,217,009 | A |   | 6/1993  | Kronberg        |          |

(Continued)

OTHER PUBLICATIONS

Brighton et al. "Treatment of Recalcitrant Non-Union With a Capacitively Coupled Electrical Field. A Preliminary Report", The Journal of Bone and Joint Surgery, 67(4): 577-585, 1985. Abstract.

(Continued)

*Primary Examiner* — Mark W Bockelman
*Assistant Examiner* — Roland Dinga
(74) *Attorney, Agent, or Firm* — Simon Kahn

(57) ABSTRACT

Osteogenesis and osseointegration promotion and maintenance devices for osseous implants include an implant member having a first electrode, an inlaid second electrode positioned on the member so that it is electrically isolated from and substantially flush with the member surface, and an electrical stimulation mechanism preferably located at the member and operative to provide electrical stimulation signals to endosseous tissue surrounding the implant through the first and second electrodes. The first electrode may be the member itself or a second inlaid electrode. The implant is thus electrically functionalized for osteogenesis and osseointgration acceleration. The device is applicable to both non-dental and dental implants. In all embodiments, the use of inlaid electrode(s) enables the general appearance, external surface and mechanical integrity of the implant to be left essentially unchanged.

17 Claims, 11 Drawing Sheets

U.S. PATENT DOCUMENTS

| | | | | |
|---|---|---|---|---|
| 5,292,252 | A | * | 3/1994 | Nickerson et al. ............ 433/173 |
| 5,383,935 | A | | 1/1995 | Shirkhanzadeh |
| 5,458,627 | A | | 10/1995 | Baranowski, Jr. et al. |
| 5,725,377 | A | * | 3/1998 | Lemler et al. ................. 433/173 |
| 5,738,521 | A | | 4/1998 | Dugot |
| 6,034,295 | A | | 3/2000 | Rehberg et al. |
| 6,120,502 | A | * | 9/2000 | Michelson .................... 606/247 |
| 6,121,172 | A | | 9/2000 | Marcolongo et al. |
| 6,143,035 | A | | 11/2000 | McDowell |
| 6,143,036 | A | | 11/2000 | Comfort |
| 6,197,450 | B1 | | 3/2001 | Nathan et al. |
| 6,214,049 | B1 | | 4/2001 | Gayer et al. |
| 6,249,191 | B1 | | 6/2001 | Forbes |
| 6,321,119 | B1 | | 11/2001 | Kronberg |
| 6,605,089 | B1 | | 8/2003 | Michelson |

OTHER PUBLICATIONS

Campbell et al. "A Constant Cathodic Potential Device for Faradic Stimulation of Osteogenesis", Medicine and Engineering Physics, 17(5): 337-346, 1995.

Chang et al. "Enhancement of Fracture Healing by Specific Pulsed Capacitively-Coupled Electric Field Stimulation", Front. Med. Biol. Eng., 3(1): 57-64, 1991. Abstract.

Cook et al. "Histologic Analysis of Retrieved Human Porous-Coated Total Joint Components", Clinical Orthopaedics and Related Research, 234: 90-101, 1988.

Fitzsimmons et al. "Frequency Dependence of increased Cell Proliferation, In Vitro, in Exposures to a Low-Amplitude, Low-Frequency Electric Field: Evidence for Dependence on Increased Mitogen Activity Released Into Culture Medium", Journal of Cell Physiology, 139(3): 586-591, 1989.

Fukuda et al. "On the Piezoelectric Effect of Bone", Journal of the Phsyical Society of Japan, 12(10): 1158-1162, 1957.

Harris et al. "Bony Ingrowth Fixation of the Acetabular Component in Canine Hip Joint Arthroplasty", Clinical Orthopaedics and Related Research, 176: 7-11, 1983.

McLeod et al. "The Effect of Low-Frequency Electrical Fields on Osteogenesis", Journal of Bone and Joint Surgery, 74(6): 920-929, 1992. Abstract.

Wiesmann et al. "Electrical Stimulation Influences Mineral Formation of Osteoblast-Like Cells in Vitro", Biochimica et Biophysica Acta, 1538: 28-37, 2001.

* cited by examiner

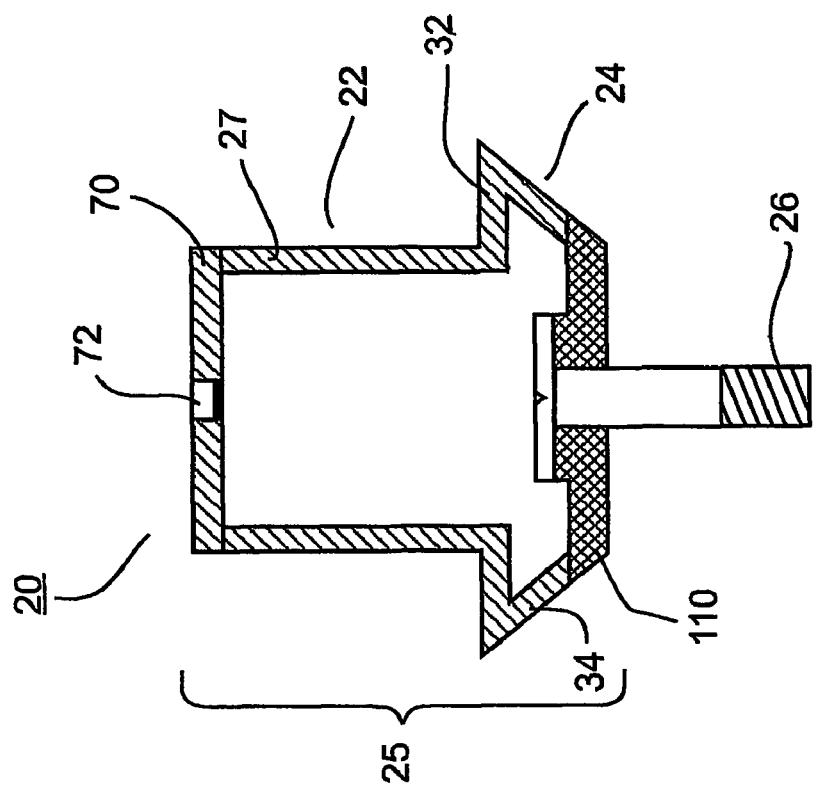
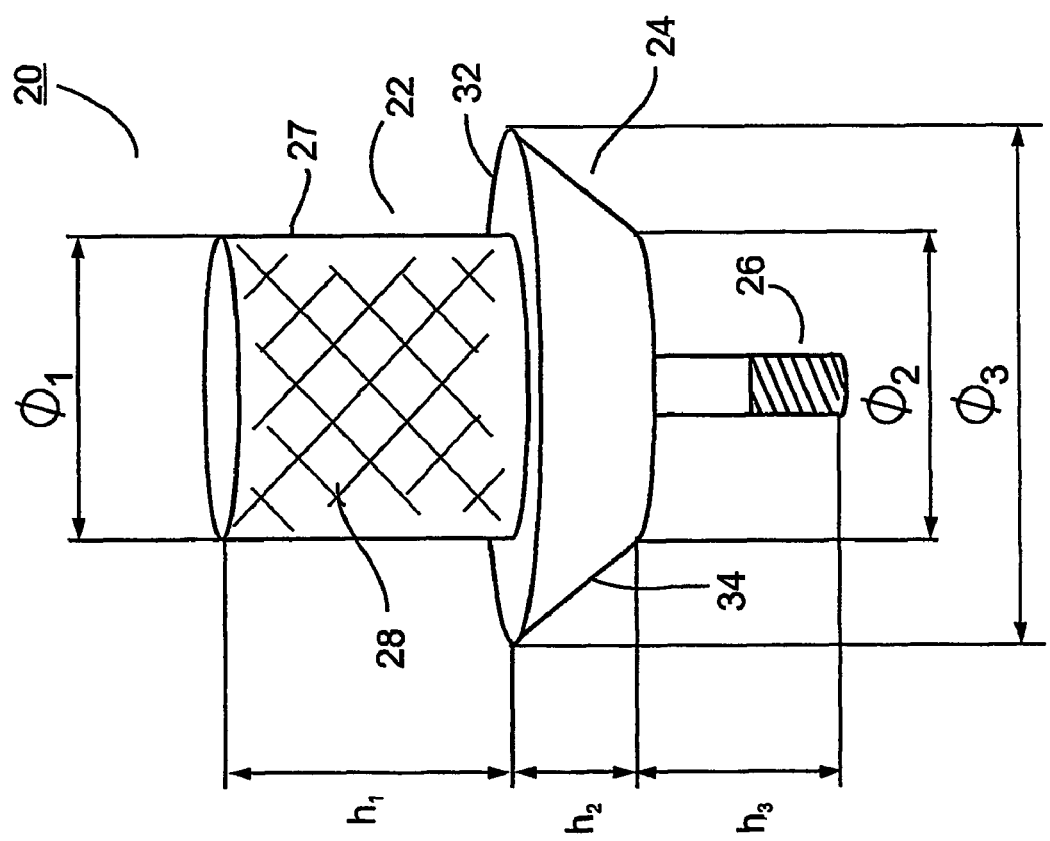
Fig. 1a
Fig. 1b

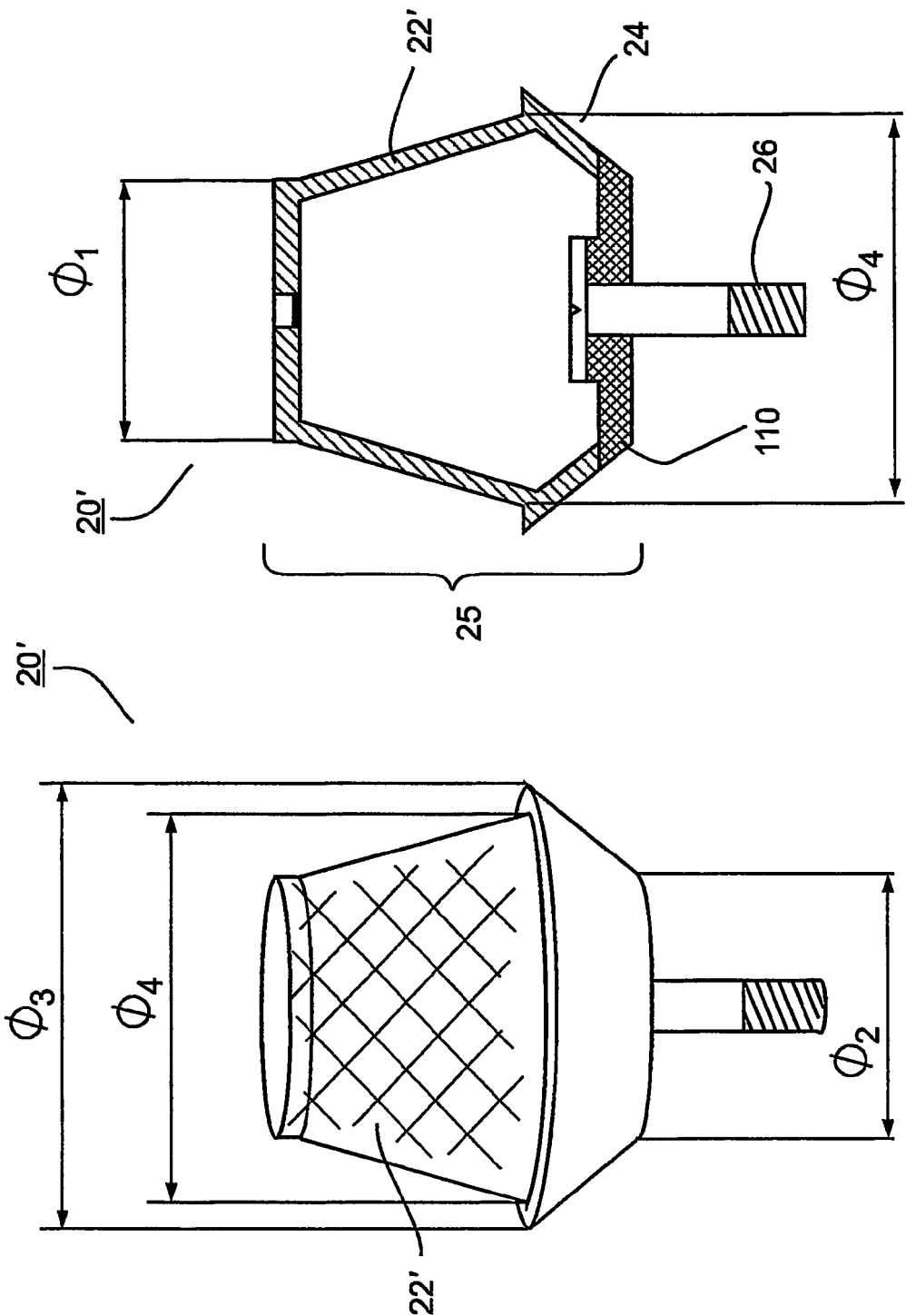

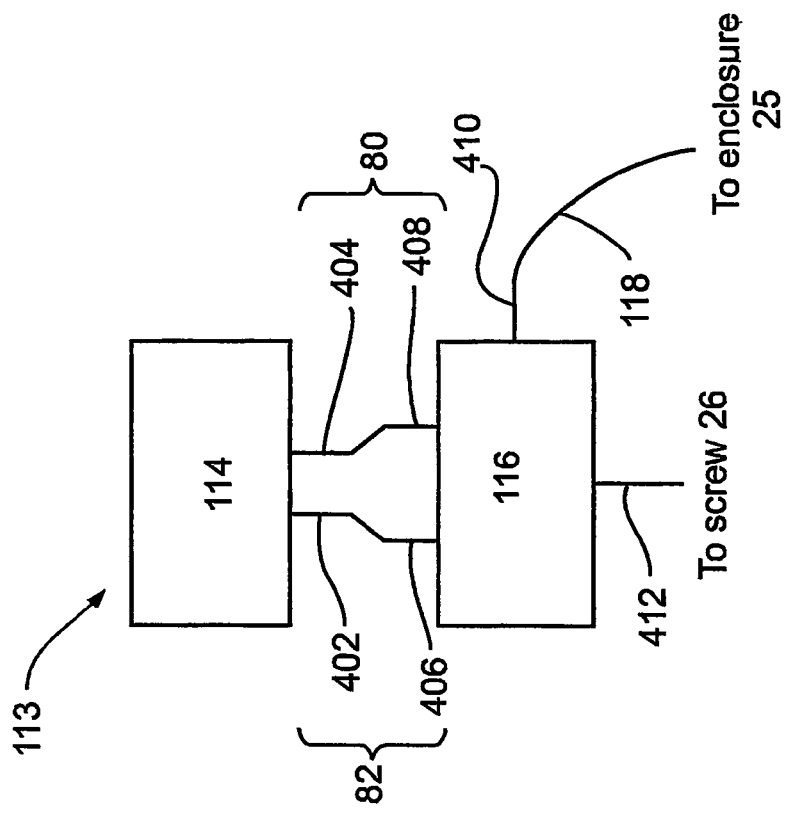
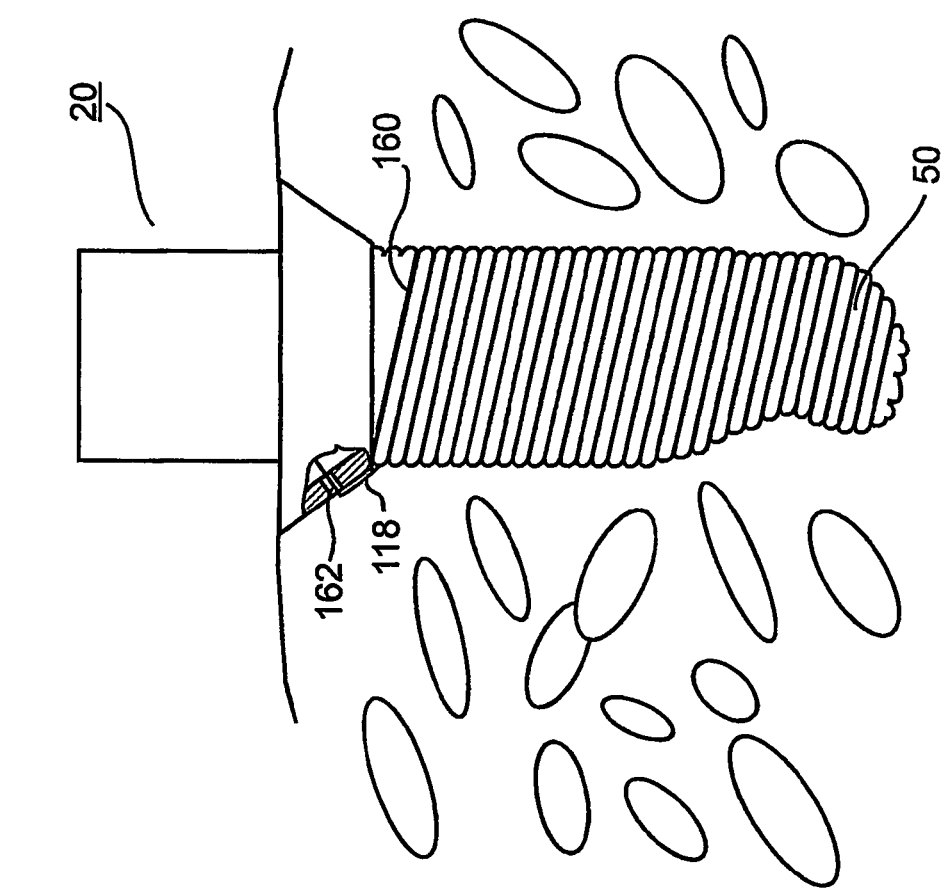
Fig. 5
Fig. 4c

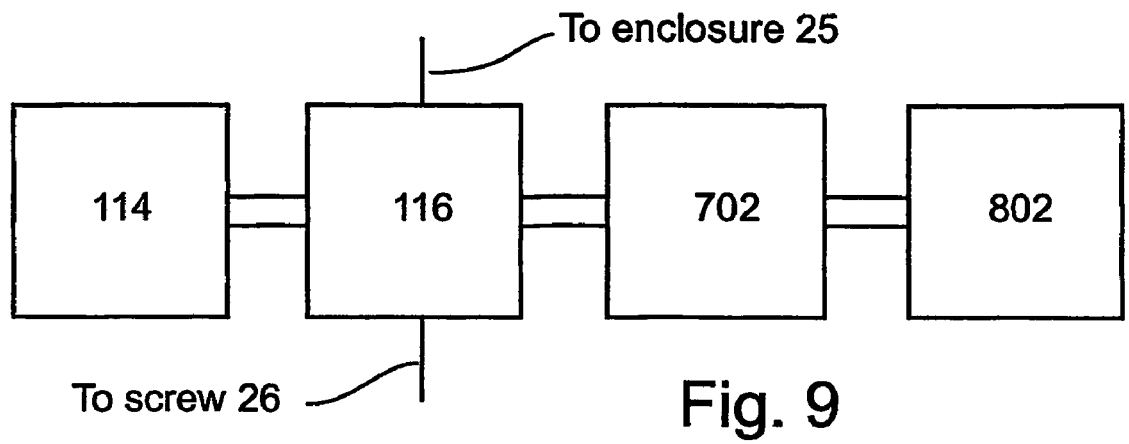
Fig. 9
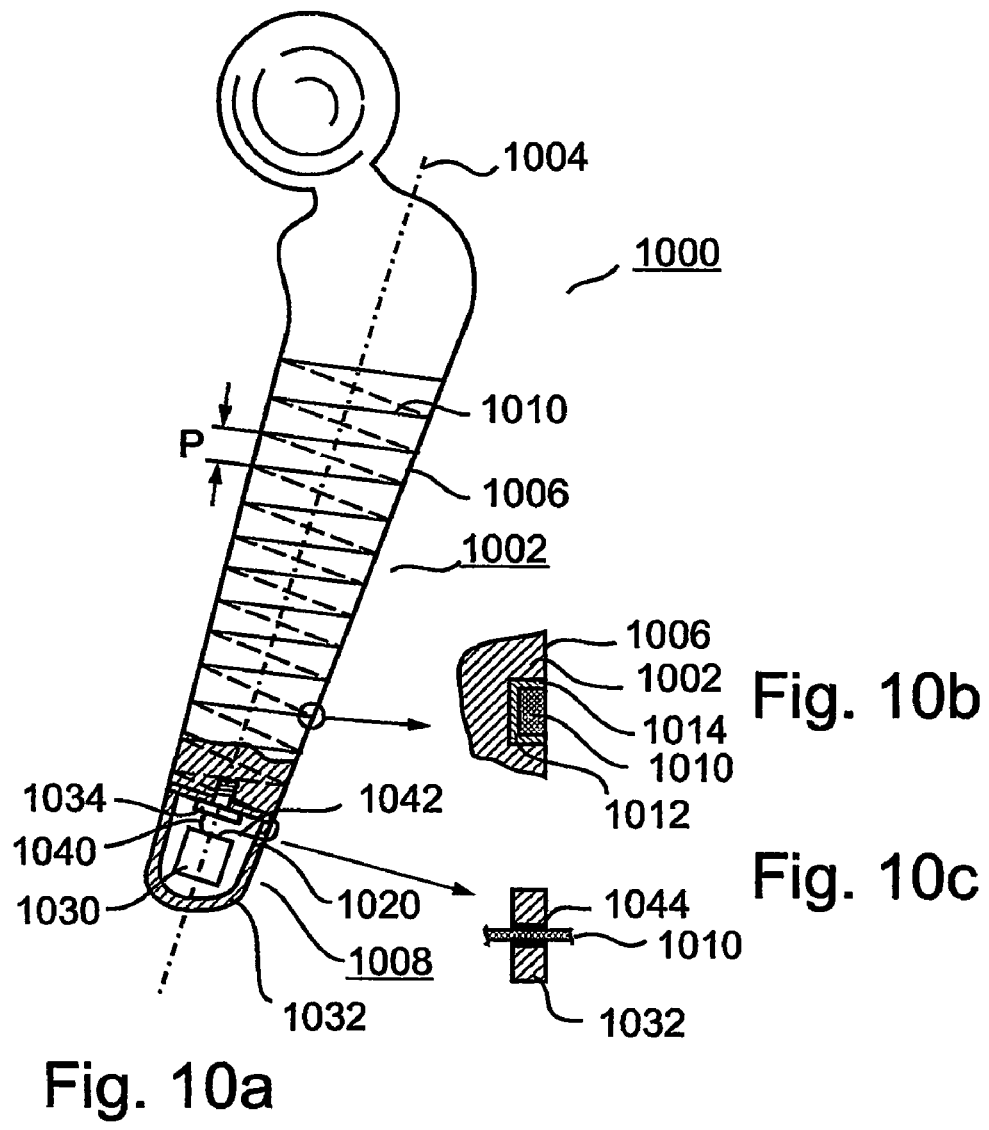
Fig. 10a
Fig. 10b
Fig. 10c

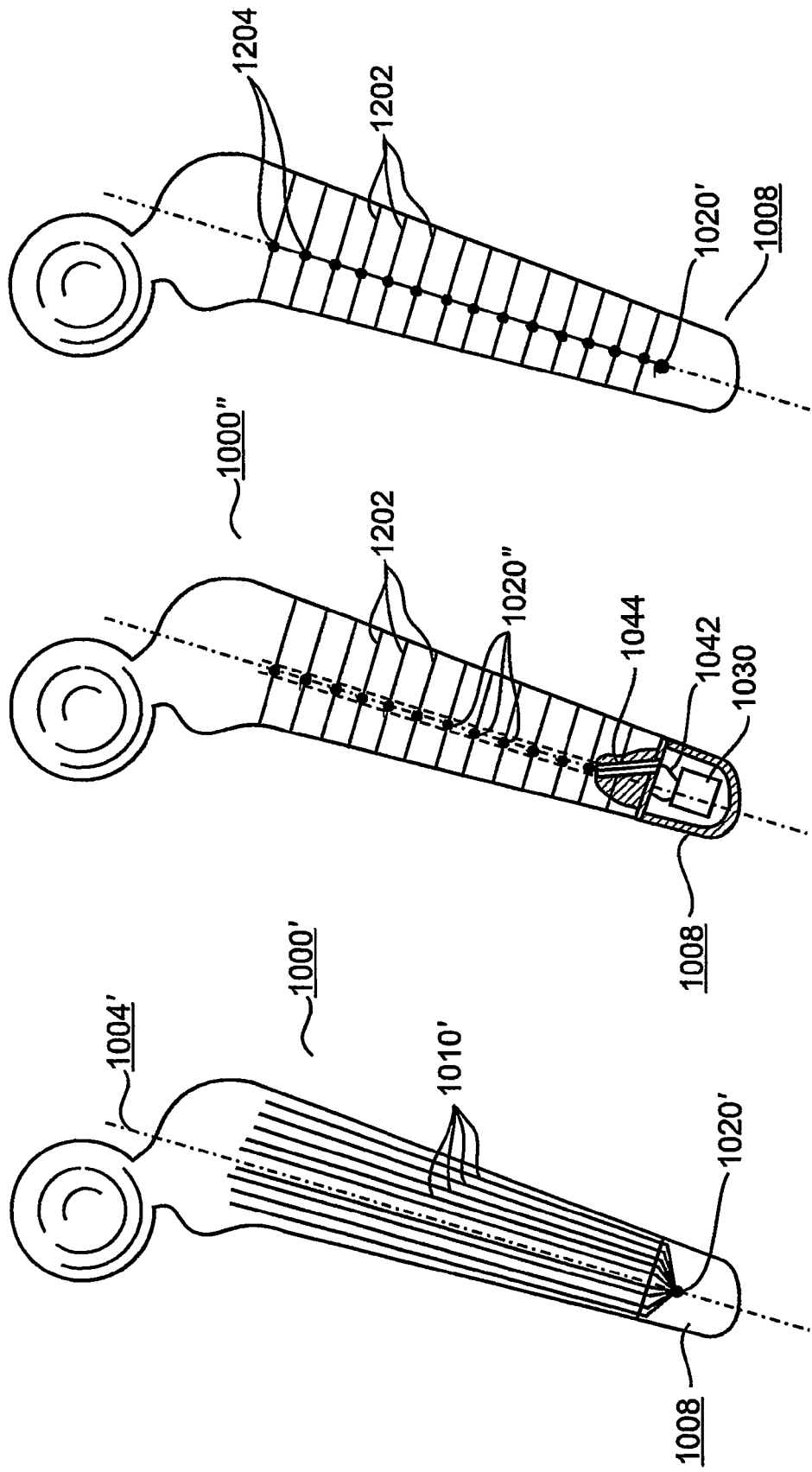

SELF POWERED OSTEOGENESIS AND OSSEOINTEGRATION PROMOTION AND MAINTENANCE DEVICE FOR ENDOSSEOUS IMPLANTS

RELATED PATENT APPLICATIONS

This application is a National Phase Application of PCT/IL2004/000092 having International Filing Date of 29 Jan. 2004, which claims the benefit of Israel Patent Application No. 154184 filed 29 Jan. 2003. The contents of the above Applications are all incorporated herein by reference.

FIELD AND BACKGROUND OF THE INVENTION

The present invention relates to processes of accelerating bone growth (osteogenesis) and bone tissue healing around endosseous implants. In particular, the present invention relates to self-powered devices incorporated in, or attached to a surgically inserted implant, for example a dental implant or a hip or knee implant, or devices having an external power source, the devices used for accelerating bone growth and healing in and around the implant surgical site. By "self-powered" we mean devices that include a built-in power source such as a battery. The following description deals in detail with both dental and orthopedic (non-dental) implants, e.g. hip implants, knee implants, etc.

A major concern for all implants, and in particular non-dental implants such as hip or knee implants, is that external appearance, feel, and mechanical integrity and function remain essentially unchanged. Moreover, a surgeon implanting for example a hip implant will prefer to stick to existing procedures even if the implant itself were altered. Presently used implants have undergone decades of development to be brought to an optimal design. The stringent requirements of implants in terms of long term function mean that this optimal design must be preserved as much as possible in any effort to "functionalize" the implant for osteogenesis and osseointegration promotion.

It is known that dental implants are widely used, and manufactured by a number of companies (e.g. Nobel Biocare USA, Inc., 22715 Savi Ranch Parkway, Yorba Linda, Calif. 92887). Dental implants replace the natural tooth roots as anchors for the restorative device. As such, they must be well integrated into the hard bone tissue. The conventional procedure for inserting a dental implant includes drilling a hole in the maxillary or mandibular jawbone, and inserting the implant in the prepared hole. Various types of endosseous dental implants are used, e.g. blades, screws, and cylinders. The implant is generally made of titanium or titanium alloy and the top of the implant is provided with mating means (usually a top portion and inner threads) for attaching the restorative device. Before attaching the restorative device, however, there is typically a healing phase of between three to six months, during which time bone tissue grows around the implant so that it becomes well integrated with the adjacent bone. This is when direct bone-to-implant interface has been achieved. However, the implant is still at a risk of failure and crestal bone loss within the first year, some of the main reasons being poor bone strength at the interface, and low bone-to-implant contact ratio. The primary goal of osteogenesis and osseointegration as related to implants is to increase bone density and implant-bone contact ratio around any new implant as a routine common clinical practice.

During the initial and primary healing phase, a cover screw is usually attached to the top of the implant to maintain the integrity of the top portion and inner threads of the implant. After the healing phase is completed and bone integration has successfully occurred, the cover screw is removed and discarded and the restorative phase of the treatment can be initiated. In the initial bone-healing phase, woven bone is formed around the implant. This type of bone is only partly mineralized, and therefore less able to withstand the high magnitude forces applied on the implant. The 3-6 month delay between the time of insertion of the implant and the time when a restoration can be made is needed in order for the woven bone to mature and mineralize. The delay is needed because it usually takes this length of time for the bone-forming cells and bone tissue surrounding the implant to mature sufficiently to adequately hold the implant, so that the final restoration will be firmly and properly anchored. This delay is a clear disadvantage of the conventional procedure in use today, leaving the patients with impaired oral function and esthetics because of the missing teeth. The goal of the restorative dentist is to restore normal function and esthetics with no delay, therefore a dual-function device is needed: 1) for osteogenesis and osseointegration promotion to fasten and ensure implantation success and 2) a prosthetic design that allows for immediate tooth restoration. Such a dual-function device is not known in the art.

It is also known that orthopedic prosthetic un-cemented components are widely used alternatives to conventional cemented prostheses. For example, a hip joint replacement offers successful rehabilitation of damaged joints. The prosthesis can be cemented or un-cemented. The cemented prosthesis is held in place in the femoral bone by acrylic polymer cement. Crack fatigue in the cement layer and osteolysis can lead to prosthesis loosening and eventual failure. In the 1980s, a new implant design was introduced, to attach directly to bone. It was hoped that cementless prostheses would solve the problems of the cemented prostheses. For un-cemented prostheses, a very exact preparation is needed because bone cannot bridge a gap of more than 2 mm.

Longer time periods are needed for the rehabilitation process because bone must be allowed to grow towards and into the prosthesis. The un-cemented prostheses are implanted in all the patient population, but are recommended mainly for younger and more active patients. The un-cemented prosthesis may become loosened if a strong bond between stem and bone is not achieved. A long-term successful bond makes the uncemented prosthesis superior to the cemented acrylic polymer-dependent prosthesis.

The un-cemented orthopedic implant also needs bone in-growth into the porous surface of the weight-bearing part of the prosthesis (W. H. Harris, "Bony ingrowth fixation of the acetabular component in canine hip joint arthroplasty", Clin. Orthop, 176; 7, 1983). Animal studies have shown that only 10% of the prosthesis surface is occupied by bone after three months. Bone ingrowth into human prostheses may be even smaller, one of the reasons being the large loads applied by the patients. Cook et al, in "Histologic analysis of retrieved human porous coated total joint components", Clin. Orthop. 234; 90 1988, have found almost no bone ingrowth into the porous surface of prostheses retrieved from human patients.

It has long been known that the application of electric currents (electric stimulation) can speed bone growth and healing. The electrical stimulation may employ faradic, inductive or capacitive signals. In the mid-1960s, C. A. L. Bassett and others measured the weak electrical signals generated by the bone itself, analyzed and reproduced those signals artificially, and used them to reverse osteoporosis or aid in the healing of fractured bones. E. Fukuda in "On the piezoelectric effect of bone", J Physiol. Soc. Jpn. 12:1158-62, 1957, and Yasuda, J. Kyoto Med. Assoc. 4: 395-406, 1953 showed that stress induced on crystalline components of bone produced current flow. Yasuda showed that similar electric signals could enhance fracture healing. Direct current capacitively coupled electric fields and alternately pulsed electromagnetic fields affect bone cell activity in living bone tissue. Friedenberg et al. in "Healing of nonunion by means of direct current", J. Trauma, 11:883-5, 1971, were the first to report healing of nonunion with exogenous current. Brighton et al, in "Treatment of recalcitrant nonunion with a capacitatively coupled electric field", J. Bone Joint Surg. Am. 65:577-85, 1985, reported 84% healing of nonunion with D.C. treatment. Time-varying current delivering electrodes have also been used in order to minimize accumulation of electrode products, while square wave patterns were shown to hasten mineralization during bone lengthening in the rabbit tibia. In his study, Brighton used capacitatively coupled electric fields to the limb by capacitor plates over the slim, and accelerated bone fracture healing.

K. S. McLeod and C. T. Rubin in "The effect of low frequency electrical fields on osteogenesis", J. Bone Joint Surg. 74a:920-929, 1992, used sinusoidal varying fields to stimulate bone remodeling. They found that extremely low frequency sinusoidal electric fields (smaller than 150 Hz) were effective in preventing bone loss and inducing bone formation. They also found strong frequency selectivity in the range of 15-30 Hz. At 15 Hz, induced electric fields of no more then 1 mV/m affected remodeling activity. Fitzsimmons et al. in "Frequency dependence of increased cell proliferation", J Cell Physiol. 139(3):586-91, 1985, also found a frequency specific increase in osteogenic cell proliferation at 14-16 Hz. Wiesmaun et al. in "Electric stimulation influences mineral formation of osteoblast like cells in vitro", Biochim. Biophys. Acta 1538(1):28-37, 2001 applied an asymmetric saw tooth wave form at 16 Hz and found enhanced biomineralization. W. H. Chang in "Enhancement of fracture healing by specific pulsed capacitatively coupled electric field stimulation", Front. Med. Biol. Eng., 3(1):57-64, 1991, showed similar beneficial results at 15 Hz to those achieved by Brighton with a 60 KHz sine-wave. Other recent references on faradic stimulation include the paper by C. E. Campbell, D. V. Higginbotham and T. K Baranowski published in Med. Eng. Phys., vol. 17, No. 5, pp. 337-346, 1995 (hereinafter CAM 95), and U.S. Pat. No. 5,458,627 to Baranowski and Black. Studies related specifically to dental bone tissue are also known, and a number of patents disclose related systems, for example U.S. Pat. No. 4,244,373 to Nachman. However, the art that relates specifically to dental bone growth stimulation by small, self powered electrical means is very limited.

U.S. Pat. No. 5,292,252 to Nickerson et al. discloses a stimulator healing cap powered by an internal small battery. The cap can be reversibly attached to a dental implant, and stimulates bone growth and tissue healing by application of a direct current path or electromagnetic field in the vicinity of bone tissue surrounding the implant, after the implant is surgically inserted. While Nickerson does not provide details of the battery, it is clear from his description that his battery is volumetrically extremely small, thus having very small capacity, which may not suffice for effective DC stimulation. Moreover, DC stimulation is known to have negative side effects. For example, Kronberg in U.S. Pat. No. 6,321,119 points out that studies on electrical stimulation of bone growth have shown that application of DC stimuli alone may be problematic in stimulating bone regeneration since bone grows near the cathode (i.e. the negative electrode), but often dies away near the anode. This phenomenon may result from electrolytic effects, which can cause tissue damage or cell death through pH changes or the dissolution of toxic metals into body fluids. Other disadvantages of Nickerson's device include: being sunken into the gingiva, it has an internal volume too small to contain a large enough battery. Its shape causes great discomfort upon removal. The healing cap is connected to the implant by a thin, weak plastic rod that may break during normal chewing. Its insulation section is larger than the battery itself, limiting the size of the battery even more.

AC (alternating current) signals may work better in electrotherapy than DC (direct current) signals, and pulse bursts may be more effective than single pulses. For this reason, many bioelectronic bone growth stimulators rely solely on AC effects, removing any net DC current from the outputs by passing the signal through a blocking capacitor. Such a capacitor forces the positive and negative output currents, when summed over a full cycle of the output waveform, to be equal, canceling each other out.

Although bone growth stimulation by AC or pulsed currents is deemed beneficial, there are no known practical, self-powered, compact dental stimulator caps using such currents. A somewhat related device disclosed by Sawyer et al. in U.S. Pat. No. 4,027,392 lacks enough description to warrant detailed discussion. Sawyer's disclosure mentions an embodiment of a bionic tooth powered by a battery and including an AC circuit that is clearly impractical: among major disadvantages, it does not appear to be removable without major surgery (since removal of his upper portion 26 occurs by unscrewing insulating member 30 from external implant thread 22, thus causing major trauma to the extensive gingival area contacted by portion 26); it uses a preferred signal frequency range of 0.5 to 1 mHz; and it cannot provide current pulses. The microcircuitry indicated by its FIG. 3 is not shown incorporated within the cap, and it is extremely doubtful that it can be implemented in the system shown. Its battery cap ("crown") is too long, penetrating deep into the gingiva (or even through the bone), thus being unfeasible and useless from a surgeon's point of view. Also, Sawyer's device is not a dual-function device, i.e. it does not serve as a temporary abutment on which one can install a temporary crown.

Another related device is disclosed by Dugot in U.S. Pat. No. 5,738,521. Dugot describes a method for accelerating osseointegration of metal bone implants using AC electrical stimulation, with a preferably symmetrical 20 µA rms, 60 KHz alternating current signal powered by a small 1.5 V battery. However, Dugot's system is not a compact, self-powered stimulator cap, but a cumbersome, externally (to the implant) wired and powered stimulator, which does not appear to be feasibly applicable to human dental implants.

Osteogenesis devices for non-dental implants include interbody fusion devices as described in U.S. Pat. No. 6,605,089B1 to Michelson. Michelson describes a self contained implant having a surgically implantable, renewable power supply and related control circuitry for delivering electrical current directly to an implant which is surgically implanted within the intervertebral space between two adjacent vertebrae. Electrical current is delivered directly to the implant and thus directly to the area in which the promotion of bone growth is desired. However, Michelson's apparatus is not an adaptation of a readily available implant, nor does it have an optimal configuration of electrodes.

Other devices are disclosed in U.S. Pat. No. 4,026,304 to Levy, U.S. Pat. No. 4,105,017 to Ryaby, U.S. Pat. Nos. 4,430, 999, 4,467,808 and 4,549,547 to Brighton, U.S. Pat. No. 4,509,520 to Dugot, U.S. Pat. No. 4,549,547 to Kelly and U.S.

Pat. No. 5,030,236 to Dean, and in a recent US patent application No 20030040806 by MacDonald.

U.S. Pat. No. 6,034,295 discloses an implantable device with a biocompatible body having at least one interior cavity that communicates through at least one opening with the surroundings of the body so that tissue surrounding the implantable device can grow through the opening; two or more electrodes within the device having terminals for supplying a low-frequency electrical alternating voltage and at least one of which is located inside the cavity. U.S. Pat. No. 5,030,236 also discloses the use of electrical energy that relies upon radio frequency energy coupled inductively into an implanted coil to provide therapeutic energy. U.S. Pat. Nos. 5,383,935, 6,121,172, 6,143,035, 6,120,502, 6,034,295, and 5,030,236 all relate to the use of various materials and forms of energy to enhance the regrowth of bone at the interface between an implanted prosthesis and the native bone. None of these devices perform satisfactory osteogenesis promotion, maintenance or acceleration while leaving the implant member or stem essentially unchanged in appearance and mechanical properties.

There is thus a widely recognized need for, and it would be highly advantageous to have, practical, self-powered osteogenesis and osseointegration promotion and maintenance devices for endosseous implants that can perform electrical stimulation using various signals. It would also be extremely advantageous that such devices, when used for example in hip or knee implants, should require minimal changes to both appearance and mechanical integrity and function of the implants. The primary goal of such devices would be to increase bone density and implant bone contact ratio around any new implant as a routine common clinical practice. In the case of dental implants, such a device should preferably serve also as an abutment for a prosthetic crown that immediately restores oral function.

SUMMARY OF THE INVENTION

According to the present invention there is provided an osteogenesis and osseointegration promotion and maintenance device for an osseous implant including an implant member having a conductive surface and operative to serve as a first electrode, an inlaid second electrode positioned on the member so that it is electrically isolated from and substantially flush with the surface, and a stimulation mechanism operative to provide electrical signals to an endosseous tissue surrounding the member through the first and second electrodes.

According to the present invention there is provided an osteogenesis and osseointegration promotion and maintenance device for an osseous implant including an implant member having a surface, a first electrode inlaid in the surface, a second electrode inlaid in the surface and electrically isolated from the first electrode, and a stimulation mechanism located at the member and operative to provide electrical signals to an endosseous tissue surrounding the member through the first and second electrodes.

According to the present invention, there is provided a self powered osteogenesis promotion device including a tissue-contacting body having an external surface in contact with biological tissue and having a hollow enclosure, a conductive element in electrical communication with the hollow enclosure and electrically isolated from the external surface, and an electrical stimulation mechanism located within the hollow enclosure for providing electrical stimulation to the biological tissue through the conductive element, wherein the electrical stimulation is enhanced stimulation.

According to the present invention, there is provided a self powered osteogenesis and osseointegration device including an implant member, an electrode positioned on the member so that the electrode is electrically isolation from a surface of the implant member, and a stimulation mechanism operative to provide electrical stimulation signals to an endosseous tissue surrounding the member through the electrode, wherein a position of the electrical stimulation mechanism of the electrode results in an essentially unchanged external appearance and mechanical integrity of the implant member.

According to the present invention there is provided a method for osteogenesis and osseointegration promotion and maintenance involving an implant member implanted in the human body, comprising electrically functionalizing the implant member while keeping its external appearance and mechanical integrity essentially unchanged, and using the electrically functionalized implant member to promote osteogenesis and osseointegration of osseous tissue with the implant member.

According to the present invention there is provided a self powered osteogenesis and osseointegration promotion and maintenance device for use with a dental endosseous implant, including a hollow enclosure having an electrically biocompatible conductive external wall in substantial electrical contact with the gingiva and insulated from the implant, a biocompatible metallic screw for reversibly attaching the enclosure to the implant, the screw electrically insulated from the external wall, and an electrical stimulation mechanism for providing electrical stimulation signals to the endosseous tissue.

According to the present invention there is provided a dual-function temporary abutment capable of osteogenesis and osseointegration promotion and maintenance and simultaneously capable of restoring post implantation oral function due to prosthetic crown-supporting design, the abutment attachable to a dental implant, including an internally hollow enclosure configured to be attached to a temporary dental crown, a metallic screw for facilitating the attachment of the abutment to the implant, the screw mechanically coupled to, and electrically insulated from the enclosure, and an electrical stimulation mechanism located preferably inside the hollow enclosure, the mechanism operative to provide stimulation signals in an external electrical path including the abutment and the implant.

According to the present invention there is provided a method for osteogenesis and osseointegration promotion and maintenance in a dental implant while restoring post-implantation oral function, including providing an electrical stimulation mechanism enclosed within a dual-function temporary abutment attachable to the dental implant, attaching a temporary dental crown to the abutment; and activating the stimulation mechanism, thereby providing a plurality of current paths between the abutment and the implant, whereby currents flowing in the current paths promote and maintain osteogenesis and osseointegration.

According to the present invention there is provided a self powered osteogenesis and osseointegration promotion and maintenance device integrated with a hip implant, including a partially hollow implant member having an electrically biocompatible conductive external envelope, at least one stimulation electrode encircling the member and insulated electrically from it, and an electrical stimulation mechanism for providing electrical stimulation signals to the endosseous tissue, the stimulation mechanism connected with one polarity to the member and with another polarity to the at least one stimulation electrode.

According to the present invention there is provided a dual-function temporary abutment capable of osteogenesis and osseointegration promotion and maintenance and simultaneously capable of restoring post implantation oral function, the abutment attachable to a dental implant, the abutment including an internally hollow enclosure, a temporary crown attached to the enclosure, means to attach the enclosure to the dental implant, and an electrical stimulation mechanism enclosed within the enclosure and operative to provide stimulation signals in an external electrical path including the abutment and the implant, whereby the stimulation promotes osteogenesis and osseointegration between the implant and an endosseous tissue, and whereby the temporary crown restores oral function immediately after the implantation.

According to the present invention, there is provided a device for osseointegration, including a titanium implantable member having a surface with a groove, and an inlaid electrode placed in the groove, a layer of titanium oxide applied to the surface, insulating the inlaid electrode from the surface, and a stimulation mechanism operative to provide electrical stimulation signals to an endosseous tissue surrounding the member through the inlaid electrode.

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described below. In case of conflict, the patent specification, including definitions, will control. In addition, the materials, methods, and examples are illustrative only and not intended to be limiting.

BRIEF DESCRIPTION OF THE DRAWINGS

The invention is herein described, by way of example only, with reference to the accompanying drawings, wherein:

FIG. 1 shows a preferred embodiment of the osteogenesis device of the present invention as implemented in dental implants in (a) isomeric view and (b) cross-section;

FIG. 2 shows another preferred embodiment of the dental osteogenesis device of the present invention in (a) isomeric view and (b) cross-section;

FIG. 5 shows a schematic diagram of a stimulation mechanism comprising a micro-battery connected to an electronic device;

FIG. 9 shows an embodiment of a stimulation mechanism that further includes activation means;

FIG. 10(a-c) shows schematically a preferred embodiment of the osteogenesis device of the present invention as applied to hip implants, having a spiral winding inlaid electrode;

FIG. 11 shows schematically another embodiment of the osteogenesis device of the present invention as applied to hip implants, having longitudinal parallel inlaid electrodes;

DESCRIPTION OF THE PREFERRED EMBODIMENTS

The present invention discloses, in various embodiments, an osteogenesis and osseointegration promotion and maintenance device (hereinafter "osteogenesis device") for endosseous implants, capable of providing DC, AC and arbitrary current train pulses, or any combination thereof. In a preferred embodiment in which the osteogenesis device is self-powered, the device preferably uses as power source an internal battery that may be miniaturized (i.e. a microbattery). The microbattery may be further integrated with electronic and/or actuating circuitry. Alternatively, the osteogenesis device can be powered remotely from outside the body. In embodiments of devices with extremely small internal cavity volumes (such as a dental implant) that cannot use conventional batteries, the internal battery is preferably a three-dimensional (3D) thin film micro-electro-chemical cell as described in U.S. Pat. No. 6,197,450 to Nathan et. al. The micro-electro-chemical cell may be integrated on the same silicon chip with the microcircuit that controls output signals. Any internal power source relevant to the present invention will hereafter be referred to as a "microbattery", while the microcircuit that controls output signals will be referred to as a "stimulation circuit or device". A power source plus stimulation device will be referred to as "stimulation mechanism". For the sake of simplicity, the term "microbattery" will be applied hereinbelow also to regular batteries that may be used internally in implants that are not small, e.g. hip or knee implants. Separate descriptions are given below for dental implants and non-dental (e.g. hip) endosseous implants that use the osteogenesis device. In some embodiments, the osteogenesis device and the implant are integrated in one piece, i.e. the osteogenesis device is an integral part of the implant. That is, the implant is modified to become a "functionalized" (for osteogenesis acceleration) implant. The principles and operation of an osteogenesis device for endosseous implants according to the present invention may be better understood with reference to the drawings and the accompanying description.

Osteogenesis Devices In Dental Implants

Figures 3, 4A:
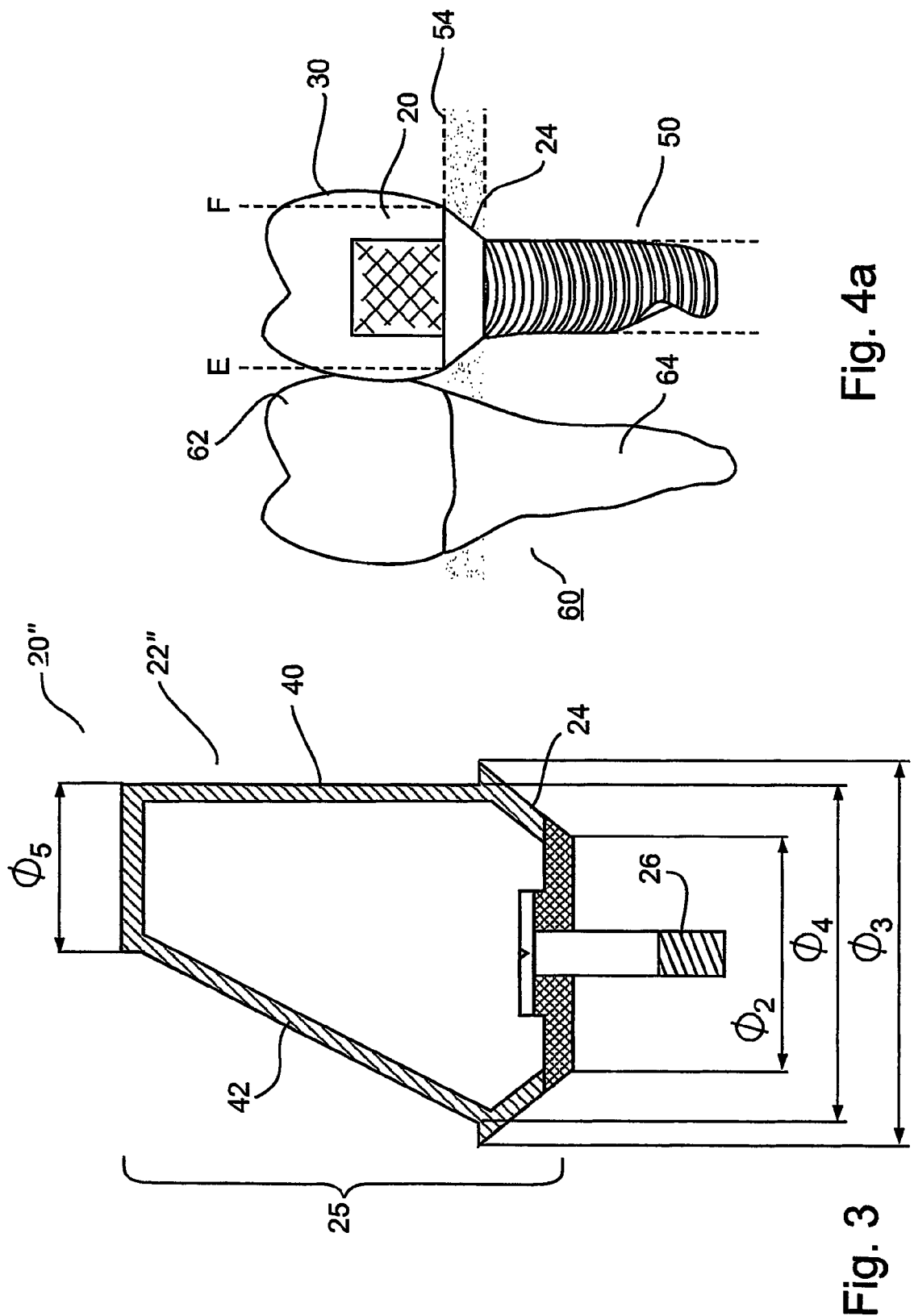
FIG. 3 shows yet another preferred embodiment of the dental osteogenesis device of the present invention in cross-section.

Referring now to the drawings, FIG. 1 shows a preferred embodiment of the osteogenesis device of the present invention, as applied to dental implants. FIG. 1 shows an isometric view of a temporary osteogenesis abutment 20 in (a) and a cross-section in (b). Temporary abutment 20 includes a top section 22, a mid-section 24 and a bottom screw section 26. In a preferred embodiment, sections 22 and 24 are made of one piece, and referred to as an "enclosure" 25 section of the abutment. Top section 22 is preferably cylindrical and internally hollow, with a height $h_1$ between ca. 3-12 mm, preferably between 3-8 mm, and most preferably around 5 mm; and diameter $\Phi_1$ of between 2.5 and 6 mm, preferably between 3.5 and 4.5 mm, and most preferably around 3.75 mm. Top section 22 has a cylindrical envelope wall 27, the same wall extending to mid-section 24 in case the two sections are integrated. For the purposes of the present invention, the optimal thickness of wall 27 is the smallest thickness still ensuring mechanical stiffness and integrity of the abutment, while bonded to a temporary crown, see FIG. 2 and description below. Typically, this thickness is about 0.5-1 mm. Height $h_1$ depends on the height of the individual tooth to be attached to abutment 20, see below. Top section 22 is preferably made of a metal used normally in present dental abutments, for example titanium, and has an external cylindrical surface 28 prepared or treated to bond to a temporary crown 30 as shown in FIG. 4a. However, section 22 may be made of other materials, such as ceramics or hard plastics, as long as it fulfills the mechanical requirements. Mid-section 24 is structured to ensure at its top plane 32 a perfect match to temporary crown 30, while its side envelope 34 is shaped to allow easy removal upon completion of function. As shown, envelope 34 is preferably conical. Section 24 may be substantially hollow internally and, as pointed out above, may integrally form an "enclosure" of one piece with top section 22, as seen in FIG. 1(a), as well as in FIGS. 2 and 3. Mid-section 24 is made of an electrically conductive rigid material, preferably a metal such as titanium. If integrated with top section 22, the top section is made preferably of the same material, and its wall must be electrically conductive in a contact area with the gingiva, see FIG. 4. Typical dimensions of envelope 34 are a small diameter $\Phi_2$ (that presents an emerging profile of the abutment from the gums) of between 3.25 to 6 mm, and most typically around 3.75 mm, a large diameter $\Phi_3$ matching the diameter of typical dental implants, currently between 5 and $\Phi_6$ mm, and a height $h_2$ of typically between 1-4 mm. Mid-section 24 is partially or fully immersed in the gum (gingiva), see FIG. 4, while top section 22 is essentially located on top of the gingiva.

Bottom screw section 26 is metallic, normally made of titanium, and essentially identical with screws typically used to attach existing abutments to dental implants, such as an implant 50 shown in FIG. 4. Screw section 26 is electrically isolated from enclosure 25 by an electrical insulating separator 110, preferably in the shape of a disc.

FIG. 2 shows in isometric view in (a) and in cross-section in (b) another embodiment of a temporary abutment 20' according to the present invention. Abutment 20' is essentially identical in all with abutment 20 of FIG. 1, except for a conical top section 22' replacing cylindrical top section 20. Conical top section 22' provides more internal volume to contain the stimulation mechanism, control means and activation means described below. Section 22' is typically of a small diameter and a height similar to those of section 22 above, while having a large diameter $\Phi_4$ close to, and no larger than $\Phi_3$.

FIG. 3 shows (in cross section only) an embodiment of a temporary abutment 20" according to the present invention wherein a top section 22" is of a combined cylindrical-conical shape, to be referred to hereafter as "angular". An angular shape is of particular importance for abutments in anterior teeth, and for abutments in anterior and posterior jaw areas because of the angulation of the teeth in the bone. The angulated abutments allow for treatment of angulated implants—a clinical situation often encountered in the maxilla (upper jaw). As made clear by the figure, top section 22" has a cylindrical envelope section 40 smoothly translating into a conical envelope section 42. A top small diameter $\Phi_5$ is now typically smaller than $\Phi_1$ while all other dimensions are essentially similar to those in FIGS. 1 and 2. The dental implant embodiment of the invention is now further described based on the embodiment of FIG. 1, with the understanding that the following description applies equally well to the embodiments of FIGS. 2 and 3.

FIG. 4 shows the abutment 20 of FIG. 1 inserted with its bottom screw 26 into dental implant 50, and its top section 22 attached to a temporary crown 30. The figure shows an isometric view in (a) and a cross-section (without a crown) in (b). FIG. 4(a) also shows an adjacent tooth 60 with a crown 62 and a root 64. In contrast with previous devices, in particular those of U.S. Pat. Nos. 4,027,392 and 5,292,252, the device of the present invention is not only a stimulation device but also a temporary crown-carrying abutment. Moreover, abutment 20 is designed to resemble as much as possible existing abutments, thus not requiring any changes in normal dental surgery procedures, while temporary crown 30 can be individually shaped for each patient. The latter is a critical requirement for such a dual-function device, and a feature that is non-existent in any of the prior art patents. Since the dual-function device (temporary abutment) of the present invention typically resembles existing abutments, its removal and replacement with a permanent crown requires advantageously a standard surgical procedure, unlike special surgical procedures needed in prior art devices.

Figure 4B:
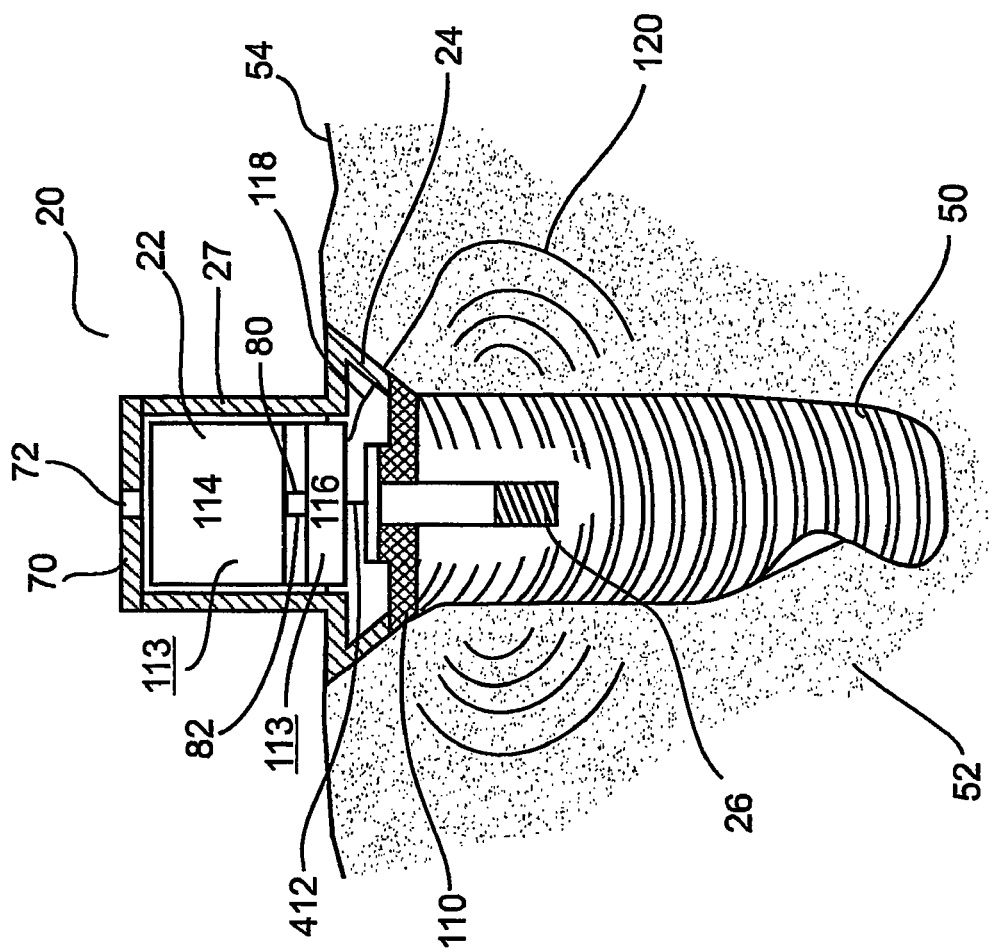
FIG. 4 shows the device of FIG. 1 inserted with its bottom screw section into a dental implant: (a) isomeric view; (b) cross-section; and (c) an active abutment connected to an implant with a single inlaid electrode.

FIG. 4(b) shows in cross section abutment 20 attached to dental implant 50 implanted in an osseous tissue 52 below gingiva 54. The figure shows the typical positioning of mid-section 24 relative to the top of a gingiva 54. Abutment 20 may in some cases stick out upwards from gingiva 54. However, in all cases, mid-section 24 maintains electrical contact with the gingival tissue.

Implant 50 is preferably a standard metal (preferably titanium) electrically conductive implant manufactured by a number of manufacturers and well known in the art. The figure shows the internal structure inside top section 22 and mid section 24, which is mechanically coupled to implant 50 through screw section 26, while electrically insulated from implant 50 by electrically insulating separator 110. In a preferred embodiment, electrically insulating separator 110 is titanium oxide. Top section 22 may optionally have a removable top plate 70 attached (e.g. screwed in) to cylindrical wall 27, and a socket 72 that may aid in opening the top plate, or removing the entire abutment from implant 50. Separator 110 is preferably of a minimal shape and size that ensure electrical isolation between screw 26 and implant 50 and sections 22 and 24, while imparting mechanical strength to the abutment-implant connection. Separator 110 may be made of any insulating biocompatible material, for example plastic such as Teflon, ceramic, glass, hard rubber, etc. The essential requirement is that mid-section 24 be at least partially in electrical contact with gingiva 54, while electrically isolated from implant 50. Separator 110 is bonded to mid-section 24 and screw 26 in a way that provides both complete sealing between the internal space inside the abutment and the outside, as well as a strong enough mechanical hold for screw 26. Such bonding and sealing may be provided by means including a ceramic seal, a metal-glass seal or a glass-epoxy seal, which are well known in the art.

As mentioned, top section 22 as well as (at least partially) mid-section 24 (i.e. enclosure 25) are internally hollow, allowing inclusion of an electrical stimulation mechanism 113 comprised of an internal micro-battery 114 and at least one electronic device 116. Using typical dimensions of $\Phi_1$=3.75 mm and wall thickness of 0.5 mm (i.e. the internal diameter of top section 22 is ca. 2.75 mm) and $h_1=8$ mm, the internal volume of section 22 is about 40-45 mm$^3$. With $h_1=5$ mm, the volume would be around 25-28 mm$^3$. Section 22' in FIG. 2 has a larger internal volume. Micro-battery 114 may be a small standard type battery, preferably a Lithium battery, or a thin film battery, preferably the micro-electro-chemical cell described in U.S. Pat. No. 6,197,450. As described in more detail in FIG. 5 below, in one embodiment, micro-battery 114 is electrically connected with both polarities to device 116 through electrical contacts 80 and 82. Device 116 is connected with one polarity through a contact 118 to the electrically conductive envelope of enclosure 25, and with another polarity, through screw 26 to implant 50. In another embodiment (not shown), micro-battery 114 may be connected with one polarity to device 116, and with another polarity to either enclosure 25 or screw 26, in which case, device 116 is connected with the other polarity to screw 26 or enclosure 25 respectively. In either embodiment, an electrical path 120 is thus established between mid-section 24 and implant 50 through the tissue composed of gingiva 54 and osseous tissue 52. Electrical path 120 is active (passing current) when micro-battery 114 is connected in the circuit comprising abutment 20, implant 50, osseous tissue 52 and gingiva 54. Path 120 is inactive (no current) when source 114 is disconnected from the circuit, preferably as a result of inputs received through device 116. One task of device 116 is to convert the DC power of micro-battery 114 into AC or pulsed voltages or currents. Another task of device 116 is to provide timing for current pulses. Yet another, optional task of electronic device 116 is to relay and perform instructions from a source external to abutment 20, to activate and de-activate path 120. Device 116 includes most preferably at least one integrated circuit acting as a stimulation circuit, and additionally and optionally as a timing/control circuit, operative to fulfill the tasks listed above, as described in more detail below.

As mentioned above, the electrical stimulation provided by device 20 through at least one electronic device 116 is preferably in the form of AC currents or pulsed DC currents. It should be apparent that any configuration of AC or DC currents may be used alone or in combination, and switching may occur between the types of current used. The conversion of direct current signals, normally provided by a constant power source in the form of a battery or a micro-electro-chemical cell, to AC or pulsed DC signals is well known in the art. In particular, various electrical circuits that perform DC to AC conversion, or generate pulses from a DC voltage or DC current source are known. Such circuits include various signal generators and waveform shaping circuits described for example in chapter 12 of "Microelectronics Circuits" by A. D. Sedra and K. S. Smith, ISBN 0-03-051648-X, 1991, pp. 841-902. Implementation of such circuits (and particularly of oscillator circuits) in integrated (IC) form is also known, for example in U.S. Pat. No. 6,249,191 to Forbes. Low voltage IC circuit architectures suitable for the purposes of the present invention include for example the LM3903 1.3V oscillator by National Semiconductor, described in Application Note 154 (AN-154) of the same company. Notice is taken that successful implementation of a combination of a micro-battery and a DC-to-AC converter or pulse generator circuit in a limited space such as the volume inside enclosure 25 has not been accomplished in prior art, and there are no known products or even prototypes of such combinations. For example, the osteogenesis promoting pulse generator disclosed in U.S. Pat. No. 5,217,009 to Kroneberg is not integrated on a chip, but mounted on a circuit board of relatively large (2.5×5.0 cm) dimensions, the final size requiring a volume of 1.7×2.5× 9.5 cm$^3$. Thus prior art pulse generators are of no use for the purposes of the present invention.

The technical requirements of a stimulation device such as electronic device 116 as relating to dental implants are preferably the following: the device should supply a voltage in the range of 1 micro-Volt to 10 Volt, and most preferably between 100 μV to 1V, with a frequency in the range of 1 Hz to 100 KHz, preferably in the range of 5 Hz to 50 Hz, and most preferably between 10 to 20 Hz; these voltages will supply an AC output current with an amplitude between 1-300 μA/cm$^2$. For a pulsed signal, the signal should be at a voltage in the general range above. Pulse burst patterns that may be effective for the purposes of the present invention are characterized for example by waveforms described in FIGS. 1, 2, 7 and 9 of U.S. Pat. No. 6,321,119 to Kronberg. For example, in FIG. 1 therein, pulse bursts are characterized by intervals 14 (representing peak voltage or current amplitude), and intervals 16 ("off"), and 18 ("on"), representing the timing between specific transitions. In the present invention, pulse bursts preferably range from continuous to patterns with "on" intervals of between 1-10 msec and preferably 5 msec, and "off" intervals of between 100 to 4000 msec, and preferably between 500 to 2000 msec. These patterns can be defined then in terms of an average frequency of between ca. 15-600 Hz, and preferably between 30-120 Hz. The low preferred frequencies disclosed herein for both AC and pulsed signals are in marked contrast with the orders of magnitude higher frequencies used in prior art stimulation systems.

FIG. 4(c) shows an embodiment of an "active abutment" using a spiral winding inlaid electrode 160, connected to stimulation mechanism 113 through a lead 118 and a feedthrough 162. Inlaid electrodes are discussed in detail with reference to non-dental implants below. Inlaid electrodes in activated implants may have any of the embodiments (in terms of inlaid electrode configurations) shown in FIGS. 10-14 below. In particular, ring, straight line, dot and double inlaid electrode configurations described therein are also suitable for active dental abutments.

FIG. 5 shows in more detail a schematic diagram of stimulation mechanism 113 of FIG. 4 comprising micro-battery 114 connected to electronic device 116. Micro-battery 114 includes two terminals of opposite polarities 402 and 404. Electronic device 116 includes two electrical input ports 406 and 408, and two electrical output ports 410 and 412. Input ports 406 and 408 are electrically connected to terminals 402 and 404, while output ports 410 and 412 are electrically connected respectively to wall 27 of enclosure 25 through contact 118 and to screw 26. Thus, in contrast with prior art internal batteries used for stimulation in implants, e.g. those of U.S. Pat. Nos. 4,027,392 and 5,292,252, battery 114 may not need to be in direct electrical contact with any part of enclosure 25 or implant 50. A key requirement of means 113 is that it completely reside inside enclosure 25. Therefore, micro-battery 114 has dimensions smaller than the internal dimensions of enclosure 25. In particular, if micro-battery 114 is a conventional battery, preferably a Lithium battery of cylindrical shape, its cylinder diameter has to be no larger than the internal diameter of the enclosure, while its height has to be sufficiently smaller than the internal enclosure height to leave space for device 116. In a preferred embodiment, battery 114 and device 116 are positioned as shown in FIG. 4, i.e. with the battery on top. However, an inverse positioning (battery 114 below device 116) as well as same plane positioning (side-by-side) of the two elements is also possible, and within the scope of the present invention.

Figure 6:
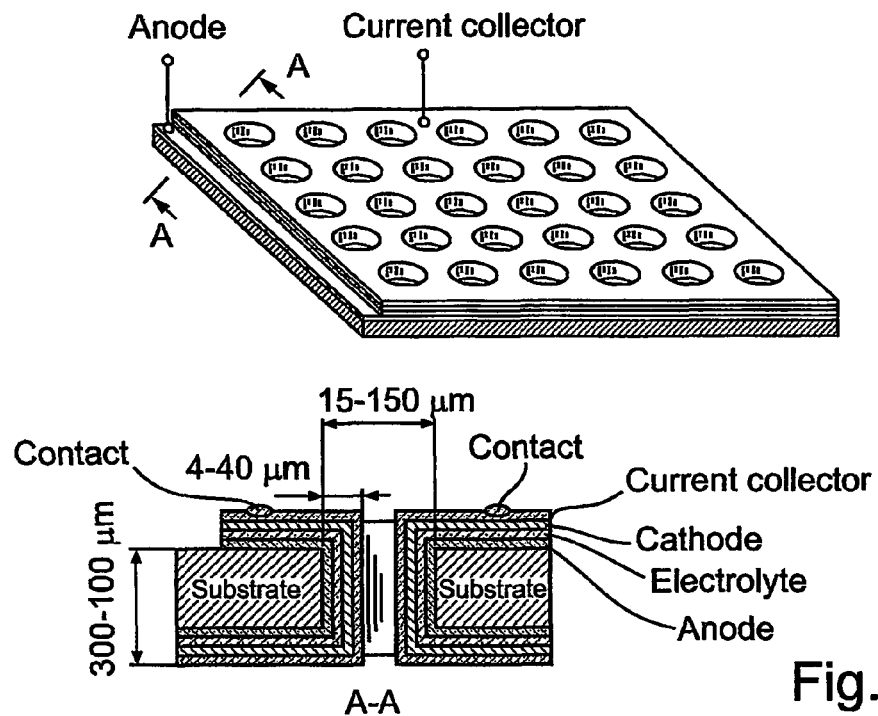
FIG. 6 shows a micro-battery from the device of FIG. 5, wherein the micro-battery is a three-dimensional thin film micro-electrochemical cell.

In a yet another preferred embodiment, shown in FIG. 6, battery 114 is a 3-D thin film micro-electrochemical cell as disclosed in U.S. Pat. No. 6,197,450. In this embodiment, cell 114 is most preferably implemented on a semiconductor substrate such as silicon or Gallium Arsenide in the form of a battery "chip". In order to fulfill the preferred power requirements above, cell 114 is typically built on a silicon or GaAs wafer of standard thickness used in microelectronic integrated circuits, i.e. 300-600 μm, with an original (before perforation) area from about 1 mm$^2$ to about 40 mm$^2$. In this embodiment, cell 114 and device 116 (which is an integrated circuit) can advantageously be packaged together using a multi-stack structure mounted on a chip scale package (CSP). CSP's are well known in the art, come in a wide variety of dimensions, materials, etc., and are described in detail for example in chapter 15 of Intel Corporation's 2000 Packaging Databook. One of the main advantages of a CSP is that its size is only ca. 20% larger than that of the chips mounted on it. Thus, the internal volume of enclosure 25 described above can easily accommodate for example the "1-Wire" CSP manufactured by Dallas Semiconductor, which has a footprint of 0.77 mm length×1.3 mm width×0.43 mm height. Other CSPs as well as other type of packages, for example the Mini SOIC package manufactured by Intel Corporation and described in the same Databook may be equally useful for the purposes of the present invention.

Figure 7:
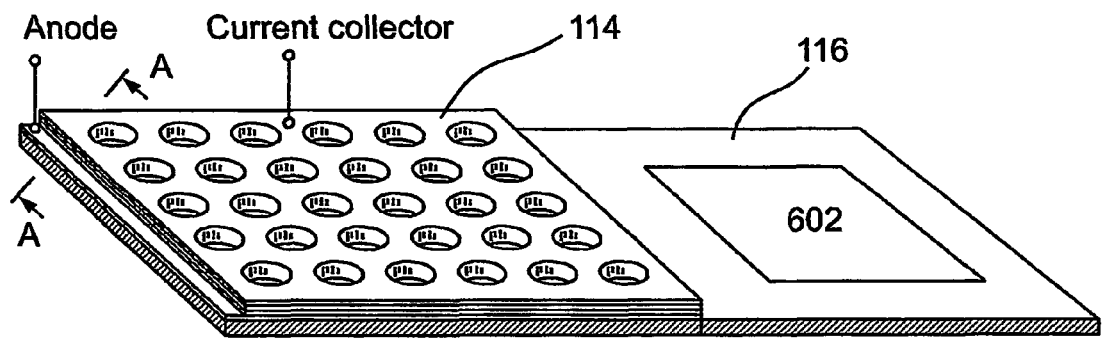
FIG. 7 shows an embodiment of a stimulation mechanism that includes a micro-electrochemical cell integrated with electronic devices.

In yet another preferred embodiment shown in FIG. 7, cell 114 is integrated on the same semiconductor chip 600 with one or more stimulation integrated circuits 602 of electronic device 116. That is, cell 114 and DC-to-AC circuits or pulse generating circuits generating the stimulation signals comprise one integrated, self-powered stimulation chip.

Figure 8:
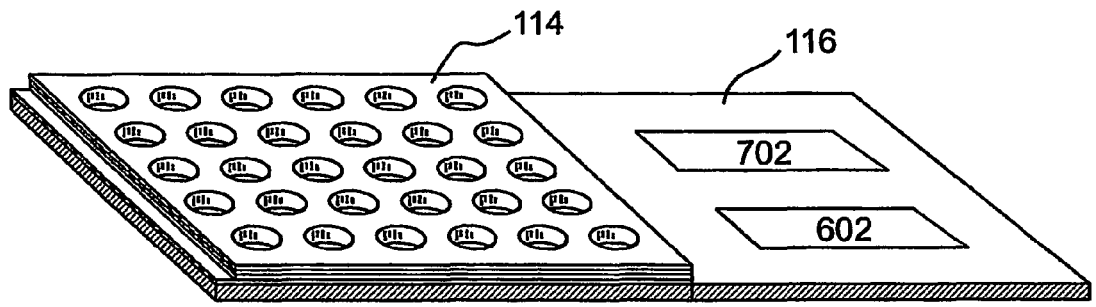
FIG. 8 shows an embodiment of a stimulation mechanism that includes control means.

As mentioned, in certain applications, it is desirable that the amplitude, timing and duration of the stimulation pulses be controllable, as described for example in U.S. Pat. No. 5,217,009 to Kronberg. Such control may be implemented by control means in the form of an integrated circuit 702, which is shown in FIG. 8 incorporated in device 116. Control circuits include various timing circuits well known in the art and described for example in Sedra and Smith above. Off-the-shelf timing circuits useful for the purposes of the present invention include the "555" family of devices by National Semiconductor Corp., for example the LM555 timer operable at 5V. The control circuitry may advantageously be integrated with the stimulation circuitry alone, or with both battery 114 and stimulation integrated circuits 602, thus providing an extremely compact device 116. Such integration is best implemented by designs and technologies known under the general mane of low-power, low-voltage, mixed signal ASICs (application specific integrated circuits). The battery, preferably a 3-D thin-film cell, and the stimulation and control circuitry, each implemented on a semiconductor integrated circuit, can advantageously be stacked and mounted together on a small-footprint package such as the CSP mentioned above.

In an alternative embodiment shown in FIG. 9, activating means 802, for example an RF, piezoelectric or magnetic element pre-programmed to receive activation orders from an external (to the mouth) activator, is added to device 116. Element 802 is used to externally effect the operation of control means 702, that is to instruct means 702 to start and stop the operation of device 116. In other words, element 802 activates or de-activates electrical path 120 upon external instructions. The activating and de-activating is best seen as, respectively, the closing and opening of the electrical connection between either one or both of the output ports of device 116 and enclosure 25 or screw 26 or both. Element 802 is of small dimensions commensurate with the internal space limitations of enclosure 25. In one embodiment, element 802 may be a thin-film piezoelectric actuator manufacturable by known thin-film processes. When such processes are compatible with the integrated process for manufacturing the integrated cell-stimulation circuit combination of FIG. 7, element 802 may be integrated with battery 114 and stimulation integrated circuits 602 on the same semiconductor chip. The actuator, as a discrete element or when implemented on an IC, is advantageously added to the stack mounted on a CSP as described above, providing a compactly packaged, self-powered combination of stimulator-control-activator device.

Osteogenesis Devices in Orthopedic (Non-Dental) Implants

FIG. 10 shows schematically a preferred embodiment of the osteogenesis device of the present invention, as applied to orthopedic implants. FIG. 10(a) shows an implant 1000 (shown exemplarily as a hip implant) made of a biocompatible material, preferably titanium. The implant has an elongated member 1002 with a length axis 1004. Member 1002 has an electrically conductive external surface 1006, and ends in an end section 1008. End section 1008 can be similar, for example, to top section 22 of dental abutment 20, described above. Essentially, end section 1008 is internally hollow, and has at least one isolated feedthrough for connecting wires therethrough. Such feedthroughs are commonly known in the art.

Preferably, the hip implant is of a size and shape provided by manufacturers of such implants. The present invention advantageously provides an osteogenesis stimulation function to such an implant with minimal external changes to its structure and mechanical properties. Typically, member 1002 is solid (full) and its conductive surface 1006 is treated and primed to provide a good surface for osteogenesis and bone tissue healing when implanted into a bone (e.g. the femur bone). Preferably and advantageously, the present invention minimizes any changes in this external surface and in the general shape of the implant, while providing the necessary electrical stimulation function to accelerate osteogenesis. The stimulation requires ideally uniformly distributed electric fields (and currents) proximate to the implant surface, the fields and currents supplied by two electrodes, surface 1006 serving as one electrode. In an embodiment having DC stimulation, surface 1006 serves as the negative electrode. In the preferred embodiment of FIG. 10, a second, thin electrode 1010, electrically insulated from surface 1006 is spun as a spiral winding in an appropriate geometry around member 1002 inside an electrically insulated groove 1012 formed in the member, preferably such that the spun electrode is externally flush with surface 1006. This electrode is thus "inlaid" in the implant, as shown in detail (b). The winding has a pitch P, which can be varied according to predetermined specifications.

Inlaid electrodes are well known in the art of integrated semiconductor circuits where they are referred to as "damascene" conductors. However, there is no known use of inlaid, "damascene" type electrodes in implants. "Damascene techniques" are well known for inlays of various metals such as gold, copper, etc in a substrate, normally but not necessarily metallic. The use of the term "inlaid" herein means to cover all geometries of an electrode conductor sunken flush into an implant member surface, preferably (but not necessarily) such that the original member surface topology remains essentially unchanged. Those skilled in the art of semiconductors will also be familiar with the term "dual damascene" used for two inlaid and overlapping conductors, isolated from each other everywhere except at a contact via. A similar "dual damascene" geometry or structure is described hereinbelow with respect to FIG. 12(c), in which however, the two conductors are electrically isolated from each other everywhere, with no conducting via.

Electrode 1010 is preferably a very thin wire or ribbon made of a biocompatible conductive material, e.g. gold or platinum, as shown in more detail in the insert in FIG. 10(b). The use of a material such as gold or platinum enables the wire to be formed with extremely small diameters, thus enabling minimization of changes in the implant surface structure. The wire may be inserted mechanically in the insulated groove, pasted in as a thick film, or deposited using various thin-film deposition techniques known in the art of damascene techniques. The insulation between electrode 1010 and surface 1006 may be provided for example by a thin insulator film 1014 deposited, inlaid, or otherwise grown (e.g. grown anodically in the case of titanium oxide on titanium) inside the groove. For a conducting member, the insulator is formed only in the groove, while the rest of the implant surface remains conducting. It is known that titanium anodic oxides may be grown to thicknesses from a few Angstroms to a few microns using techniques well known in the art, and provide excellent electrical isolation. Alternatively, the insulation may be provided by an inlaid biocompatible non-conductor, such as a thin plastic, polymer or ceramic sleeve. Advantageously, an inlaid electrode in the embodiments of FIGS. 10 and 11 (see below) needs only one point of contact to one lead of the internal power source, as discussed further below. This simplifies the design, by requiring only one electrical feedthrough 1020 in end section 1008, as shown in (c). It should be noted that the use of titanium oxide can in itself enhance bone ingrowth, as is known in the art. Thus, the use of titanium oxide as an insulator may serve two purposes: to insulate, and at the same time to provide additional osseointegration effects.

FIG. 11 shows an embodiment in which an inlaid electrode 1010' is formed as lines substantially parallel with length axis 1004 and commonly connected to one lead of stimulation mechanism 1030 (shown in FIG. 10c) through a single feedthrough 1020' in member end section 1008. It will be apparent to one skilled in the art that the lead can be split either internally or externally to the member body, so that not all lines 1010' are connected to the same single split lead. In particular, when split internally, there may be more than one feedthrough through the member end section, each feedthrough containing one split lead which then connects to one or more lines 1010'. If the member surface is non-conductive, the "line" electrodes may be split into two sets of alternating lines comprising a "first" and a "second" electrode, each set (electrode) connected through a separate feedthrough and separate lead to the stimulation mechanism (not shown). In this way, a non-conductive material may be used for the implant, while still maintaining a dual electrode system.

Figure 12C:
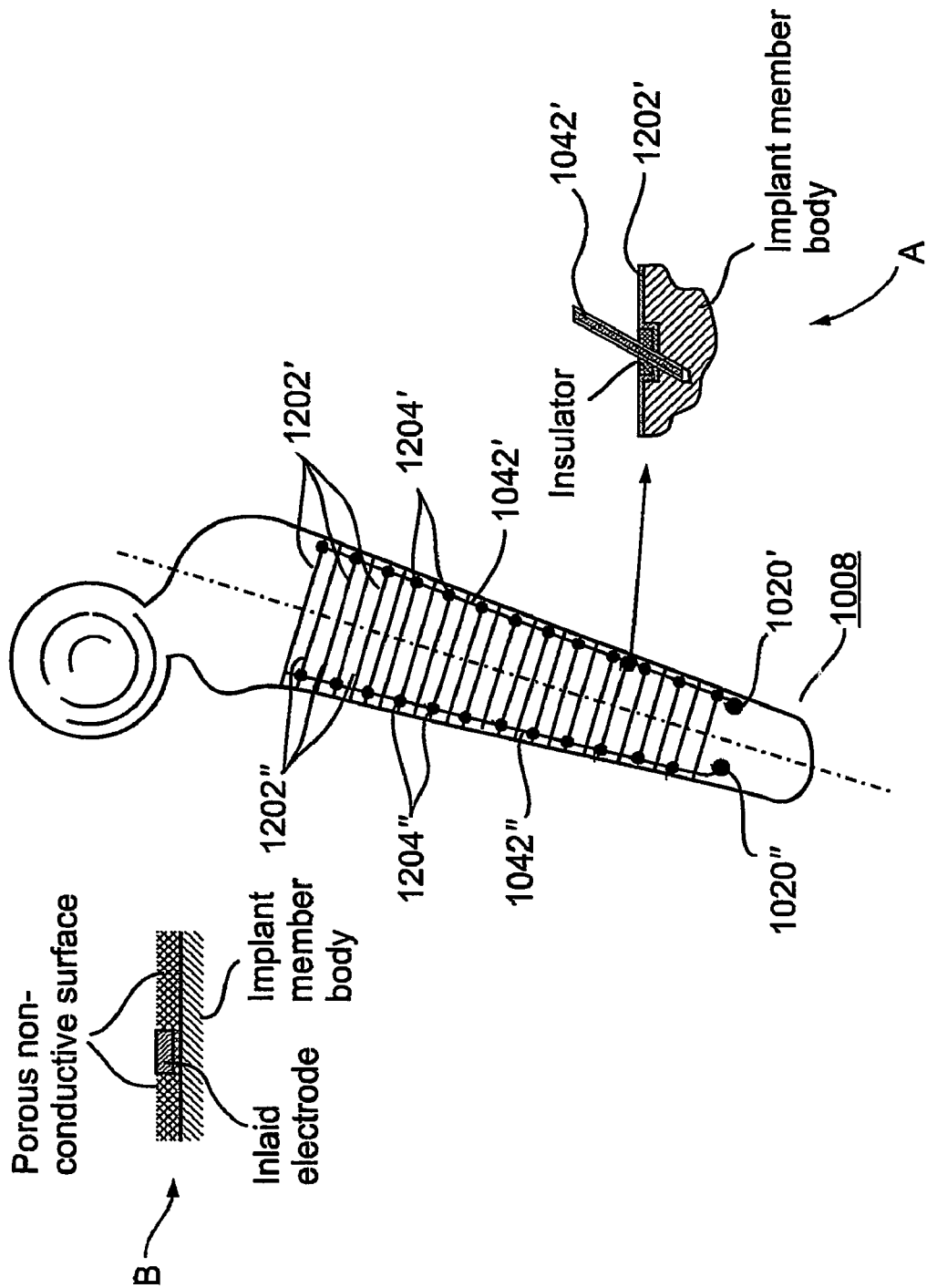
FIG. 12(a-c) shows various embodiments of the osteogenesis device of the present invention as applied to hip implants, having ring inlaid electrodes: a) rings connected to common internally threaded lead; b) rings connected to common an external inlaid lead; and c) separate ring sets connected respectively to a first and a second external inlaid lead.

FIG. 12(a-c) shows various embodiments of the osteogenesis device of the present invention as applied to hip implants, having ring inlaid electrodes: a) rings connected to a common internally threaded lead; b) rings connected to a common external inlaid lead; and c) separate ring sets connected respectively to a first and a second external inlaid lead. In FIGS. 12(a) and (b), the inlaid electrode is formed of separate rings 1202 positioned along a member 1000" substantially in a plane perpendicular to the member length axis. In these embodiments, each ring is separate and requires a separate isolated feedthrough 1020" in the member wall to connect to the common internally (FIG. 12(a)) or externally (FIG. 12(b)) threaded stimulation mechanism lead 1042, threaded through an internal isolated channel 1044 in the implant member. In FIG. 12(c), there are two sets of inlaid electrodes 1202' and 1202", staggered so that each ring 1202' lies between two 1202" rings and vice-versa. Each set of rings is connected to a common lead (1042' and 1042" respectively), each lead connected through a feedthrough (1020' and 1020") to the stimulation mechanism in end section 1008. Electrical shorts between a lead crossing a ring are prevented by an insulator layer as shown in insert A, formed for example by local deposition of a thin insulating film on the bottom (in the example ring 1202') conductor. The configuration in FIG. 12(c) removes the need to have the member itself as an electrode, for example in the case when it is non-conductive or not conductive enough. One example of a non-conductive member is shown in cross-section in insert B: a titanium member may for example have a thick enough porous titanium oxide layer on the surface, formed to enhance mechanical bonding of the member to the bone tissue. In this case, an inlaid electrode may be inlaid in the oxide layer. The electrode external surface may be substantially flush with the external surface of the oxide, thus presenting a very minor disturbance to the normal appearance, feel and function of the implant member. In other words, the exterior texture of the implant is essentially unchanged from that of a regular (not electrically functionalized) implant. A similar "double inlaid electrode" configuration may be provided using two of the spiral windings of FIG. 10, running parallel to each other such that they do not ever cross each other (not shown). More generally, the double inlaid electrode geometry may be applied to any embodiment described herein, in the case the implant member itself is either non-conductive or not conductive enough to serve as an electrode.

Figure 13:
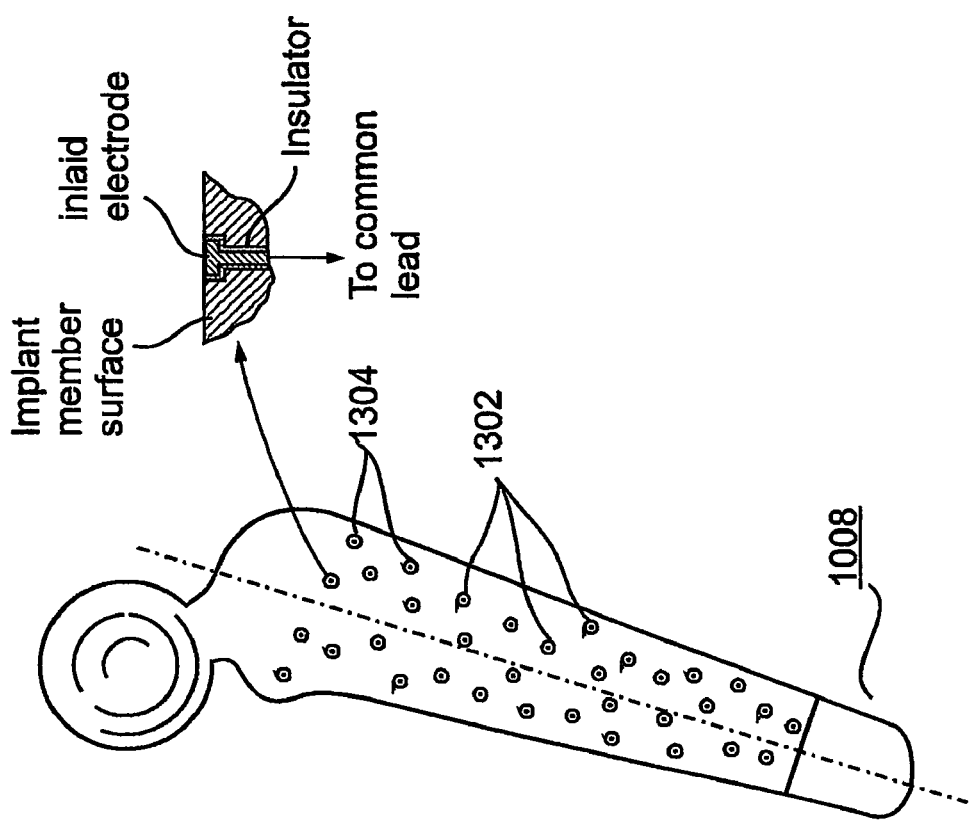
FIG. 13 shows yet another embodiment of the osteogenesis device of the present invention as applied to hip implants having separate dot inlaid electrodes.

FIG. 13 shows yet another embodiment in which an inlaid electrode is formed of separate dots 1302 distributed arbitrarily on the implant in a manner operative to provide an optimal current distribution in the tissue. As in the embodiment of FIG. 12, a separate isolated feedthrough 1304 in the member wall is needed to connect each dot to the common stimulation mechanism lead. The common lead may extend from the power source of the stimulation mechanism through an internal small-bore insulated hole 1044 that runs the length of the member, meeting at appropriate points lateral holes leading to the feedthroughs (not shown). The formation of internal bores inside a solid member, and the formation of thin insulating layers inside small bores (for example by chemical vapor deposition) are well known in the art.

It will be apparent to one skilled in the art that the shape, dimensions, pitch (or the distance between parallel lines in FIG. 11 or rings in FIG. 12 and electrical properties of the thin wire or ribbon electrode can be chosen such that they provide the required stimulation in response to an electrical input (voltage or current). For example, the wire diameter or the largest dimension in its cross section may vary from a few microns to a few mm The pitch may also vary (depending on the wire diameter) from being slightly larger (e.g. by a few microns) than the wire diameter to about 1000 times the wire diameter. It will also be apparent that the electric field and current distribution in the tissue in contact with the implant may be mapped using calculations or simulations. Accordingly, the optimum configuration of the inlaid electrode may be determined for every required stimulation condition. Advantageously, the inlaid electrode of the present invention causes minimal changes in the mechanical strength of the implant, since only a minimal amount of material is removed to form the groove in which the inlaid electrode is positioned. The thickness of the insulator may vary from being as thin as a few tens of Angstroms to any thickness. Accordingly, the groove must be larger (in either width, depth, or both) by at least a few tens of Angstroms and up to a few tens of microns than the wire diameter or width. It is apparent, as mentioned with reference to FIG. 4(c), that the inlaid electrode, in its various embodiments, may be used equally well in dental implant members.

A major advantage in having an end section 1008 housing the stimulation mechanism is that in the normal use of an orthopedic implant, this section is not functionally important. That is, the end section of e.g. a hip implant does not normally have to bind to the bone. In the embodiments of FIGS. 10-13, section 1008 is hollow, with an internal space configured to contain stimulation mechanism 1030 comprised of a power source (either a battery or energy storage means for coupling to external power generators, see e.g. U.S. Pat. Nos. 4,549, 547 and 4,467,808 to Brighton) and a stimulation electronic device. In general, the stimulation mechanism described in detail with reference to dental implants may serve as well in non-dental implants. Section 1008 has a non-conducting envelope 1032 and is connected to member 1002 through a conductive mechanical element 1034, e.g. a screw screwed into member 1002. In this case, electrical lead 1040 is connected to the member through element 1034.

Alternatively, end section 1008 may in essence be similar to the dental abutment described in detail above in its various embodiments, being now connected to a non-dental implant (member 1002) instead of a dental implant member. In this case, the electrical connections to the member body and to the inlaid electrode(s) can similarly be done through, respectively, screw 1034 and feedthrough 1020. If envelope 1032 is not electrically isolated from member 1002, the inlaid electrode may be formed also on the end section, after the feedthrough surface is properly treated to form an insulator 1044 that isolates the envelope from the inlaid electrode. Preferably, the shape and size of the end section is designed so that it minimally affects the surgical procedure.

It is appreciated that although the placing of the stimulation mechanism in an end section of an implant member is an advantageous design choice, the stimulation means may be alternatively placed in a different hollow section of the implant member. Moreover, it would be appreciated that, in certain embodiments, the stimulation mechanism may be entirely external to the implant, for example implanted separately near the implant member, or projecting the stimulation signals to the electrodes from outside the body.

Returning now to FIGS. 12 and 13, rings 1202 and dots 1302 are preferably made of gold, platinum, or any other suitable highly conductive biocompatible substance. As in the embodiments of FIGS. 10 and 11, the rings are preferably flush with the external surface of the member and have the same texture and feel, thus causing minimum disturbance in the surface texture as compared with a regular implant.

As orthopedic (e.g. hip) implants are normally much larger than dental implants and abutments, the stimulation mechanism for orthopedic implants may be in general similar to those in typical modern heart pacemakers, in both size and function. That is, an internal power source may preferably be a lithium battery of the type used in pacemakers, and the electronic device that provides the required electrical signals to the electrodes includes control means. These means may include an integrated circuit microprocessor operative to receive external (to the body) instructions, for example by RF signals, and circuits designed to provide a variety of signal waveforms to perform electrical stimulation. Stimulation mechanisms described in prior art, e.g. in U.S. Pat. No. 6,605, 089B1 to Michelson, may also be used in the orthopedic implants of the present invention.

Figure 14:
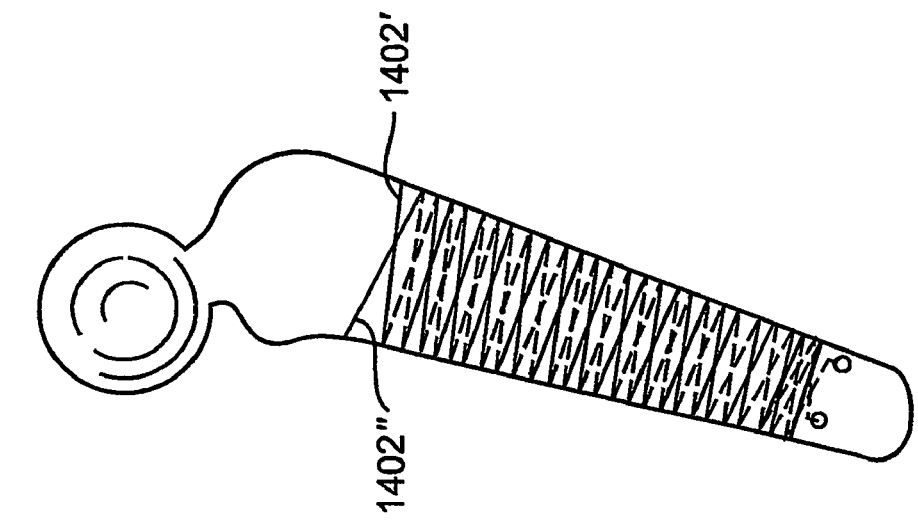
FIG. 14 shows an embodiment of the osteogenesis device for a hip implant with two crisscrossed helix inlaid electrode on a non-conductive surface.

FIG. 14 shows another embodiment of a functionalized implant in which (as in FIG. 12(c)) the implant member is not conductive enough to serve as an electrode. This embodiment uses two inlaid electrodes 1402' and 1402" that crisscross each other. In the overlapping sections, the structure is similar to the "dual damascene" structure described with reference to insert A in FIG. 12(c).

Figure 15:
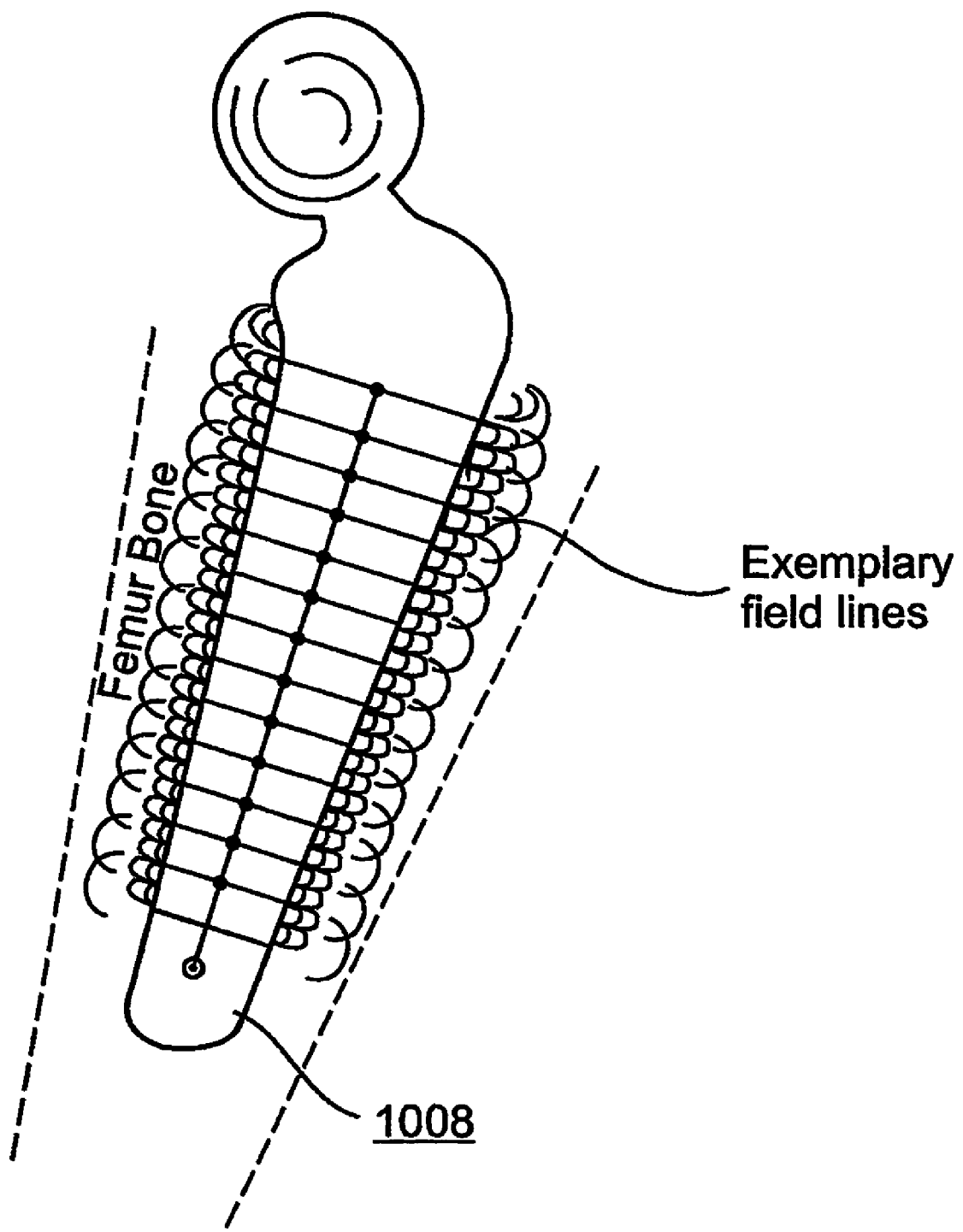
FIG. 15 shows the device of FIG. 10 in an embodiment in which the functionalized implant uses direct currents to induce osteogenesis.

FIG. 15 shows the device of FIG. 10 in an embodiment in which the functionalized implant uses direct currents to induce osteogenesis. In this case, the body (member 1002) is held at a negative bias relative to the inlaid electrode. Once implanted in the body, the stimulation mechanism is activated to provide DC currents in a plurality of electrical paths 1502 established externally to the implant between the inlaid electrode and the member. In other embodiments in which the functionalized implant uses AC and pulsed currents to induce osteogenesis, the stimulation mechanism includes similar circuits to those described above, and their preferred parameter ranges are similar to those disclosed above for the dental implant. As with heart pacers, the various electrical parameters ("on", "off", length of various stimulation cycles, etc) are externally controllable.

All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention.

While the invention has been described with respect to a limited number of embodiments, it will be appreciated that many variations, modifications and other applications of the invention may be made. For example, although the description focuses on dental and hip implants, other implants, specifically other orthopedic implants and in particular knee implants may equally well be implemented with devices as described above.

What is claimed is:
1. A dual-function abutment comprising:
a top section configured for attachment to a temporary dental crown;
a substantially conically shaped middle section exhibiting a top plane defining the conical base and a side envelope extending away from said top plane towards a bottom of said middle section, the diameter of said top section no more than the diameter of the conical base of said middle section;
an electrical insulating separator secured to the bottom of said middle section;
a metallic bottom screw section extending through said electrical insulating separator, said metallic bottom screw section mechanically coupled to, and electrically insulated from said middle section by said electrical insulating separator; and
an electrical stimulation mechanism constituted of a power source and an electronic device in communication with the power source, said electrical stimulation mechanism exhibiting a pair of electrical contacts of opposing polarity, a first of said electrical contacts electrically connected to said metallic bottom screw, and a second of said electrical contacts connected to said middle section, said top section, middle section, electrical insulating separator and metallic bottom screw section together form- ing an enclosure of a sealed inner space, said electrical stimulation mechanism ensconced within said sealed inner space, wherein said electrical stimulation mechanism is arranged to provide stimulation signals in an external electrical path including said middle section and an implant connected to said metallic bottom screw section.

2. The dual-function abutment of claim 1, wherein said stimulation signals include voltage signals selected from the group consisting of alternating voltages and pulsed voltages.

3. The dual-function abutment of claim 2, wherein said voltage signals are in the range of 1 micro-Volt to 10 Volt.

4. The dual-function abutment of claim 2, wherein said voltage signals produce alternating currents with a frequency in the range of 1 Hz to 100 KHz.

5. The dual-function abutment of claim 2, wherein said voltage signals produce alternating currents with a frequency in the range of 5 Hz to 50 Hz.

6. The dual-function abutment of claim 2, wherein said voltage signals produce alternating currents with a frequency in the range of 10 Hz to 20 Hz.

7. The dual-function abutment of claim 1, wherein said electrical insulating separator is constituted of titanium oxide.

8. The dual-function abutment of claim 1, wherein said top section exhibits one of a cylindrical shape, a conical shape and a combined cylindrical-conical shape.

9. The dual-function abutment of claim 1, wherein said top section and said middle section are constituted of a metal.

10. The dual-function abutment of claim 9, wherein said metal is titanium.

11. The dual-function abutment of claim 1, wherein said electrical stimulation mechanism comprises:
a power source;
an electronic device in communication with said power source; and
a control means connected to said electronic device and arranged to provide control signals to said electronic device,
said electronic device arranged to adjust parameters of the provided stimulation signals responsive to said control means.

12. The dual-function abutment of claim 11, wherein said parameters comprise pulse amplitude and pulse duration.

13. The dual-function abutment of claim 11, wherein said electrical stimulation mechanism further comprises:
an activating means in communication with said control means, said control means responsive to said activating means to alternately activate said electrical stimulation mechanism to provide the stimulation signals and de-activate said electrical stimulation mechanism so as to cease said stimulation signals.

14. The dual-function abutment of claim 13, wherein said electrical stimulation mechanism is mounted on a chip scale package.

15. The dual-function abutment of claim 1, wherein said electrical stimulation mechanism is mounted on a chip scale package.

16. An assembly comprising:
a dual-function abutment comprising:
a top section configured for attachment to a temporary dental crown;
a substantially conically shaped middle section exhibiting a top plane defining the conical base and a side envelope extending away from said top plane towards a bottom of said middle section, the diameter of said top section no more than the diameter of the conical base of said middle section;
an electrical insulating separator secured to the bottom of said middle section;
a metallic bottom screw section extending through said electrical insulating separator, said metallic bottom screw section mechanically coupled to, and electrically insulated from said middle section by said electrical insulating separator;
an electrical stimulation mechanism constituted of a power source and an electronic device in communication with the power source, said electrical stimulation mechanism exhibiting a pair of electrical contacts of opposing polarity, a first of said electrical contacts electrically connected to said metallic bottom screw, and a second of said electrical contacts connected to said middle section; and
a temporary crown attached to said top section,
said top section, middle section, electrical insulating separator and metallic bottom screw section together forming an enclosure of a sealed inner space, said electrical stimulation mechanism ensconced within said sealed inner space,
wherein said electrical stimulation mechanism is arranged to provide stimulation signals in an external electrical path including said middle section and an implant connected to said metallic bottom screw section.

17. The dual-function abutment of claim 2, wherein said voltage signals are in the range of 100 micro-volts to 1 volt.

\* \* \* \* \*